United States Patent [19]

diZerega

[11] Patent Number: 4,734,398

[45] Date of Patent: Mar. 29, 1988

[54] FOLLICULAR REGULATING PROTEIN

[75] Inventor: Gere S. diZerega, Pasadena, Calif.

[73] Assignee: University of Southern California, Los Angeles, Calif.

[21] Appl. No.: 23,893

[22] Filed: Mar. 9, 1987

Related U.S. Application Data

[63] Continuation of Ser. No. 475,416, Mar. 15, 1983, abandoned.

[51] Int. Cl.$^4$ .................. A61K 37/00; C07K 15/00
[52] U.S. Cl. ............................ 514/2; 514/21; 514/800; 514/843; 530/300; 530/350; 530/853
[58] Field of Search ............... 514/2, 21, 800, 843; 530/300, 350, 853

[56] References Cited

PUBLICATIONS

F. De Jong et al, Nature, vol. 263, 71–73, 1976.
diZerega, Gere S., et al., "Identification of Protein's Secreted by the Preovulatory Ovary which Suppresses the Follicle Response to Gonadotropins", Journal of Clinical Endocrinology and Metabolism, 54(6) (1982), pp. 1091–1096.
diZerega, Gere S., et al., "Identification of Proteins in Pooled Human Follicular Fluid which Suppress Follicular Response to Gonadotropins", Journal of Clinical Endocrinology and Metabolism, 56(1) (1983), pp. 35–41.
diZerega, Gere S., et al., "Human Granulosa Cell Secretion of Protein(s) which Suppress Follicular Response to Gonadotropins", Journal of Clinical Endocrinology and Metabolism, 56(1) (1983), pp. 147–155.

Primary Examiner—J. R. Brown
Assistant Examiner—John W. Rollins
Attorney, Agent, or Firm—Nilsson, Robbins, Dalgarn, Berliner, Carson & Wurst

[57] ABSTRACT

A protein moiety having a molecular weight of from 12,000 to 15,000 inhibits aromatase levels, stimulates 3$\beta$-ol dehydrogenase levels and modulates the formation of mature ova substantially independently of steroidal sex hormones. The moiety may be isolated from follicular effluent or produced by granulosa cell cultures.

9 Claims, 37 Drawing Figures

FOLLICULAR REGULATING PROTEIN

The U.S. Government has rights in this invention under Clinical Investigator Award HD-00401 and NIH Grant HD-05932.

This is a continuation of co-pending application Ser. No. 06/475,416 filed on Mar. 15, 1983, now abandoned.

FIELD OF THE INVENTION

This invention relates generally to the field of biochemistry, and more particularly to the chemistry and physiology of the ovarian cycle.

BACKGROUND AND SUMMARY OF THE INVENTION

The ovary is the essential female reproductive organ in which eggs are produced. In vertebrates there are commonly two ovaries, suspended from the dorsal surface of the broad ligaments, one on each side of the uterus. Adult human ovaries are composed of a fibrous vascular stroma in which are imbedded the Graafian follicles, which contain the eggs. The eggs are discharged by the bursting of the Graafian follicles on the surface of the ovary and are then immediately received into the mouth of the oviduct. Thereafter, the eggs flow through the fallopian tube to the uterus, covered by a mucous membrane known as the endometrium, where the fertilized ovum develops.

The egg cells or ova are periodically matured in the ovaries at intervals of approximately four weeks. At the end of each four week period, one egg reaches maturity and passes into one of the fallopian tubes. The egg descends gradually and remains viable for a short while, and during this time fertilization may take place.

Within the ovary, there is a layer of cells called the germinal epithelium. Here, the potential egg begins its existence and continues to develop until a primary follicle, i.e., a group of cells isolated from the main layer, is formed around the potential egg. During a lifetime, each human ovary forms between 200,000 and 400,000 follicles. Of all these potential eggs only a few develop into mature eggs, most of them degenerating. The primary follicle that does not degenerate increases in size, and the egg cell itself enlarges up to thirty times its original size.

Other changes occur in the areas adjacent to the follicle. As the follicle matures, it moves toward the surface of the ovary and when the maturation process is complete, the follicle protrudes from the surface. At this time, ovulation occurs, i.e., the follicle bursts and the egg is expelled from the surface of the ovary.

The developing follicle produces sex hormones by metabolizing pre-hormones using a series of enzymes: $3\beta$-ol dehydrogenase, $17\alpha$-hydroxylase, hydroxysteroid dehydrogenase, and aromatase. Aromatase is a central enzyme in the production of female sex hormones (estradiol, estrone and estriol).

These estrogenic hormones play a particularly important role in both the menstrual cycle and the reproductive cycle. Although $17\beta$-estradiol is the principal estrogenic hormone, a number of other estrogenic substances have been isolated, including estriol and estrone. These hormones induce the growth of the vaginal epithilium, secretion of mucous by the glands of the cervix and initiate the growth of the endometrium.

The corpus luteum, which fills a ruptured Graafian follicle in the mammalian ovary, produces at least three hormones, progesterone, $17\beta$-estradiol and relaxin. Progesterone acts to complete the proliferation of the endometrium, which was initiated by the estrogenic hormones, and to prepare it for the implantation of the ovum.

This reproductive cycle is well regulated as long as the production and secretion of both the sex hormones from the ovaries and the gonadotropic hormones of the pituitary gland are within normal limits. The anterior lobe of the pituitary, by manufacturing and secreting the gonadotropic hormones, controls the production of the sexual hormones in the ovaries and stimulates the development of the reproductive organs and the maintenance of their structure. The ovaries, under control of the gonadotropic hormones, produce the female sexual hormones. In turn, the rate of production of gonadotropins by the pituitary is influenced by the production of sex hormones. The effects are mutual and the two glands maintain an exact balance in hormone production.

More specifically, the follicle-stimulating hormone (FSH) from the pituitary stimulates the Graafian follicles, which thus produce estrogens. Estrogens not only inhibit FSH production through negative feedback on the pituitary, but also stimulate the pituitary to increase its production of luteinizing hormone (LH) through positive feedback. This hormone (LH) in turn brings about ovulation of the Graafian follicle. After the ovum is discharged, the LH stimulates the empty follicle, now the corpus luteum, to produce progesterone. This hormone brings about the changes in the reproductive organs required for the development of the embryo. The progesterone then partly inhibits the pituitary from producing more LH. Thus, there is no further ovulation. The subsequent fall in progesterone then releases the pituitary inhibition allowing for the production of FSH to begin the process anew.

When pregnancy occurs, the placenta of the embryo itself produces human chorionic gonadotropin (hCG), which stimulates the continuing production of progesterone from the corpus luteum, thus preventing menstruation and stimulating the continuing development of the uterus. This progesterone also inhibits further ovulation in spite of the presence of the hCG from the placenta.

Th gonadotropic hormones have been determined to be proteins, with variable amounts of carbohydrates, and their structures are known. The molecular weight of human LH is about 26,000, and that of human FSH is about 30,000. The cellular response to gonadotropic hormones is translated through cellular receptors. These receptors are located within the cell membrane and are specific for each gonadotropin, thus, LH only activates LH receptors and FSH only activates FSH receptors.

Non-abortifacient means for the avoidance of pregnancy include oral contraceptive medications which contain estrogen and/or progesterone-like steroidal sex hormones. These medications, by raising the level of sex hormones in the blood stream, generate a cervical mucous which is hostile to spermatazoa. With increased levels of such hormones the endometrium tends to resist implantation of the fertilized ova. Further, oral contraceptives directly inhibit the pituitary production and release of LH and FSH. As such, the ovarian cycle is disrupted and ovulation does not occur. The complications of such steroidal contraceptive medimedications, e.g., nausea, vomiting, weight gain, hypertension and tumor stimulation, adverse effects on calcium and phosphate metabolism, are well known and need not be discussed at length. However, these side effects result not only from the abnormally high levels of steroidal hormones in the blood stream, but from disruption of the hormonic homeostasis of the organism, i.e., the cycle of hormone adjustment between the ovary and the pituitary gland.

Accordingly, it has been a desideratum to provide a contraceptive medication which permits the regulation of the ovarian process without an accompanying disruption of the hormonic homeostasis of the organism.

The present invention accomplishes the foregoing objectives by providing a protein moiety which regulates the maturation of ovarian follicles and the production of a viable ovum without elevating the normal level of sex hormones in the body.

Specifically, a protein moiety having a molecular weight of from about 12,000 to about 15,000 daltons and an isoelectric point of from about 4.5 to about 6.5 inhibits the activity of aromatase in follicular granulosa cells, stimulates the activity of $3\beta$-ol dehydrogenase which is similarly produced, inhibits the development of granulosa cell LH receptors, and prevents the normal maturation of follicles to a mature ova. The term protein moiety, as used herein, refers to a protein, proteins or functional operatives groups thereon which produce the described results. The production and activity of the protein moiety is interspecies, and it is both produced and effective in monotocous and polytocous mammals. In another aspect of the invention, antibodies are provided to inhibit the natural production of the protein moiety with a corresponding decrease in $3\beta$-ol dehydrogenase and increase in aromatase activity resulting in the promotion of follicular development and ovum maturation. Thus, the fertility of mammalian females may be controlled substantially independently of exogenous sex steroids. Further, a method is provided for the isolation, purification and production of the protein moiety, and for the use thereof in conception control.

DETAILED DESCRIPTION OF THE PREFERRED EMBODIMENT

Figure 1:
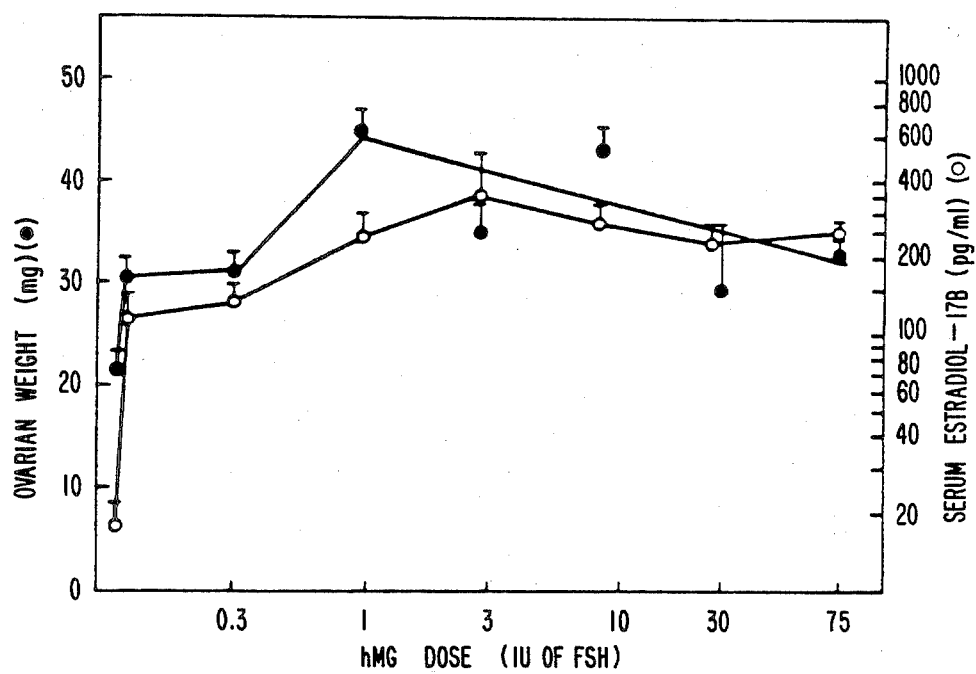
FIG. 1 describes the dose response of hypophysectomized, twenty-three-day old DES -treated rat ovaries to hMG therapy. Ovarian weight (●) and the peripheral serum $17\beta$-estradiol concentration (○) responded by achieving maximal levels with hMG doses of 1 and 3 IU, respectively.

The embodiment hereinafter set forth relates to the isolation and purification of the follicular protein moiety and its use in the inhibition of the production of the aromatase enzyme, stimulation of 3β-ol dehydrogenase production, regulation of mature ova formation and the production of the protein moiety by granulosa cell cultures.

The protein moiety is isolated from ovarian venous effluent, and human and porcine follicular fluid by methods such as salt fractionation and dialysis and purified by lyophilzation and chromatography Granulosa cells are cultured to produce substantial amounts of the protein moiety, which is then similarly purified.

The biological effect of the moiety is assessed in laboratory animals by determining variations in ovarian weight and analyzing body fluids for steriod hormone and enzyme levels. Aromatase inhibition was determined by incubating granulosa cells in the presence of a substrate and the follicular protein, and measuring the amount of estrogren formed. The 3β-ol dehyrogenase was found to be stimulated by similar methods. The addition of labelled LH and FSH to in vitro granulosa cell culture showed a decrease in LH receptors in the cells, and no charge in FSH receptors.

Regularly ovulatory primates were exposed to the follicular protein moiety and in all instances the ovarian cycle wad modified, along with follicular growth, as evidenced by estrogen and progesterone levels, without the concomitant alteration of LH and FSH levels. In subsequent cycles, the primates had timely menstrual onset and showed no toxic treatment effects. Pharmaceutically effective amounts may be administered to pregnable individuals by injection or other means known to those skilled in the art. A particularly advantageous method of administration comprises the introduction of an effective amount of moiety, in the form of a suppository, to the absorbent membranes which are adjacent the uterus.

Since the protein inhibits aromatase and normal follicle maturation, it plays a central role in the ovulatory process. Accordingly, blockage of the proteins activity allows for the maturation of multiple follicles to ovulatory status. The protein may be coincubated with hybrid cells in vivo to produce antibodies to proteins from different species. The antibody produced by the rat hybrid cultures and collected by chromatography and may be injected into previously anovulatory infertile females thus blocking the action of the follicular protein and allowing for development and eventual ovulation of one or more follicles.

Agricultural uses of a similarly prepared antibody allow for the maturation of multiple follicles in livestock which could be collected, fertilized in vitro and reinserted into a properly prepared surrogate.

EXAMPLE ONE

Identification of Follicular Inhibitory

Protein(s) in Ovarian Venous Blood

Ovarian venous blood (5 ml) was collected from six women (aged 26, 28, 31, 36, 37 and 41 years) undergoing laparotomy for indications not related to ovarian dysfunction on days 12–14 after the onset of the last menstrual period. Patients 1–3 maintained regular menstrual cycles, while patients 4–6 were anovulatory, as evidenced by oligomenorrhea and a lack of large antral follicles in the ovarian cortex. A 25-gauge needle was inserted into the venous drainage within the infundibulo-pelvic ligament, and free-flowing blood was aspirated. In addition, the locus of the preovulatory follicle was determined by direct visual inspection. Peripheral serum (10 ml) was collected concurrently from an antecubital vein. Serum was separated by centrifugation (800 x g for fifteen minutes) of the clotted specimen and stored frozen ($-35°$ C.) until fractionation. Concentrations of 17$\beta$-estradiol in ovarian (1340, 886, and 470 pg/ml) and peripheral (248, 261, and 201 pg/ml) venous samples collected from patients 1, 2 and 3, respectively, were consistent with the preovulatory 17$\beta$-estradiol levels reported for normal women. In addition, comparable samples from anovulatory patients 4–6 contained low levels of 17$\beta$-estradiol in both ovarian (less than 200 pg/ml) and peripheral (less than 50 pg/ml) sera. Slowly thawed serum was fractionated by the dropwise addition of an equal volume of saturated ammonium sulfate under persistent agitation at 4° C. After twelve hours, the precipitate was resuspended (2:1, vol/vol) with 10% ammonium sulfate. After twelve hours of additional agitation and centriguation (3000 x g for 30 minutes), the supernatant was dialyzed with 10,000 molecular weight exclusion membranes against Dulbecco's phosphate-buffered saline (PBS; 0.025 M; pH 6.8) for 16 hours. The retentate was passed through a Concanavalin A-linked Sepharose 4B (Con A) column (5 ml; Pharmacia, Piscataway, N.J.) which was washed with 5 vol 0.5 M NaCl, pH 7.4, then further eluted with 0.5 M $\alpha$-methyl-D-mannoside in PBS at a flow rate of 20 ml/h at 4° C.

None of the fractions eluted from the Con A column by $\alpha$-methyl-D-mannoside contained inhibitory activity in the rat bioassay. Therefore, only the results of eluents obtained from the nonbound material will be presented. Additional fractionations were performed where indicated on a Sephadex G-25 (superfine) column (1.6$\times$50 cm; Vo=60 ml; 5 ml/h; 4° C.) with PBS. All Sephadex molecular weight seiving was performed using a reverse flow technique. Both Sephadex G-50 and G-25 were prepared according to the instructions of the manufacturer and equilibrated in the elution buffer. To increase resolution, the smallest of the Sephadex beads were removed by direct pipetting of the surface before degassing and column packing (10 mm H$_2$O). Protein elution profiles were determined using an ISCO absorbance meter at 254 nm.

The activity was assessed in twenty-three-day-old Sprague-Dawley rats (45–55 g) 2 days after hypophysectomy which were kept at 25° C. with intervals of fourteen hours of light and ten hours of darkness. Animals were caged in groups of three and given rat chow and water ad libitum. Silastic implants containing DES (diethylstilbestrol) were prepared as follows. Ten grams of Silastic (TM) polymer were mixed with 3 g DES for thirty minutes at 16° C.; thereafter, four drops of stannous octoate catalyst were added, with an additional ten minutes of mixing. The material was passed through a Luer-lock syringe (id, 1 mm) into a streaming (95° C.) 0.9% NaCl water bath and annealed for two hours. DES-containing Silastic implants (1$\times$5 mm) were inserted sc in the hypophysectomy incision forty-eight hours before assay. The assay design consisted of three rats at each dose of reference preparation and unknown. Forty-eight hours after hypophysectomy, animals were given either varying concentrations of gonadotropins (LH:FSH, 1:1) dissolved in 0.15 M NaCl with 1% bovine serum albumin and/or equal volumes of test fractions in two divided daily doses. Twenty-four hours after the initial injection, animals were sacrificed by decapitation, and ovaries were removed, trimmed and weighed on a Roller-Smith balance. Rat trunk serum 17$\beta$-estradiol determinations were performed by methods described in Goeblesmann et al., in Leprow et al (Eds.) *Vasectomy: Immunological and Pathologic Effects in Animals and Man*, Academic Press, New York, p. 165. Control determination of chromatography fractions containing inhibitory activity was performed by heating (56° C.; for thirty minutes) or trypsin digestion (20 mg/100 ml) of representative samples for 4 hours.

The ovarian weight and serum 17$\beta$-estradiol responses of the rats to human menopausal gonadotropin (hMG), are depicted in FIG. 1. Over the range tested (0.3–75 IU hMG; 1 IU hMG=1 IU FSH), the change in ovarian weight was a function of the hMG dose. The initial ovarian weight before injection was 21.2$\pm$0.9 mg (mean$\pm$SEM), which increased to 31.2$\pm$1.2 mg after 0.1 IU hMG, reaching a maximum at the 1 IU hMG dose (46$\pm$1.4 mg). These values are comparable to those previously reported. The rat serum 17$\beta$-estradiol levels was 17$\pm$1.4 pg/ml, increasing to 120$\pm$2.4 pg/ml with 0.1 IU hMG, thereafter reaching maximum levels (385 +47 pg/ml) in a linear dose-response relationship at 3 IU. One international unit of hMG injected every twelve hours for two days was chosen as the challenge regimen in the bioassay. The increase in ovarian weight was in partial response to the increase in the number and size of antral follicles, as evident by the appearance of the ovaries.

Figure 2:
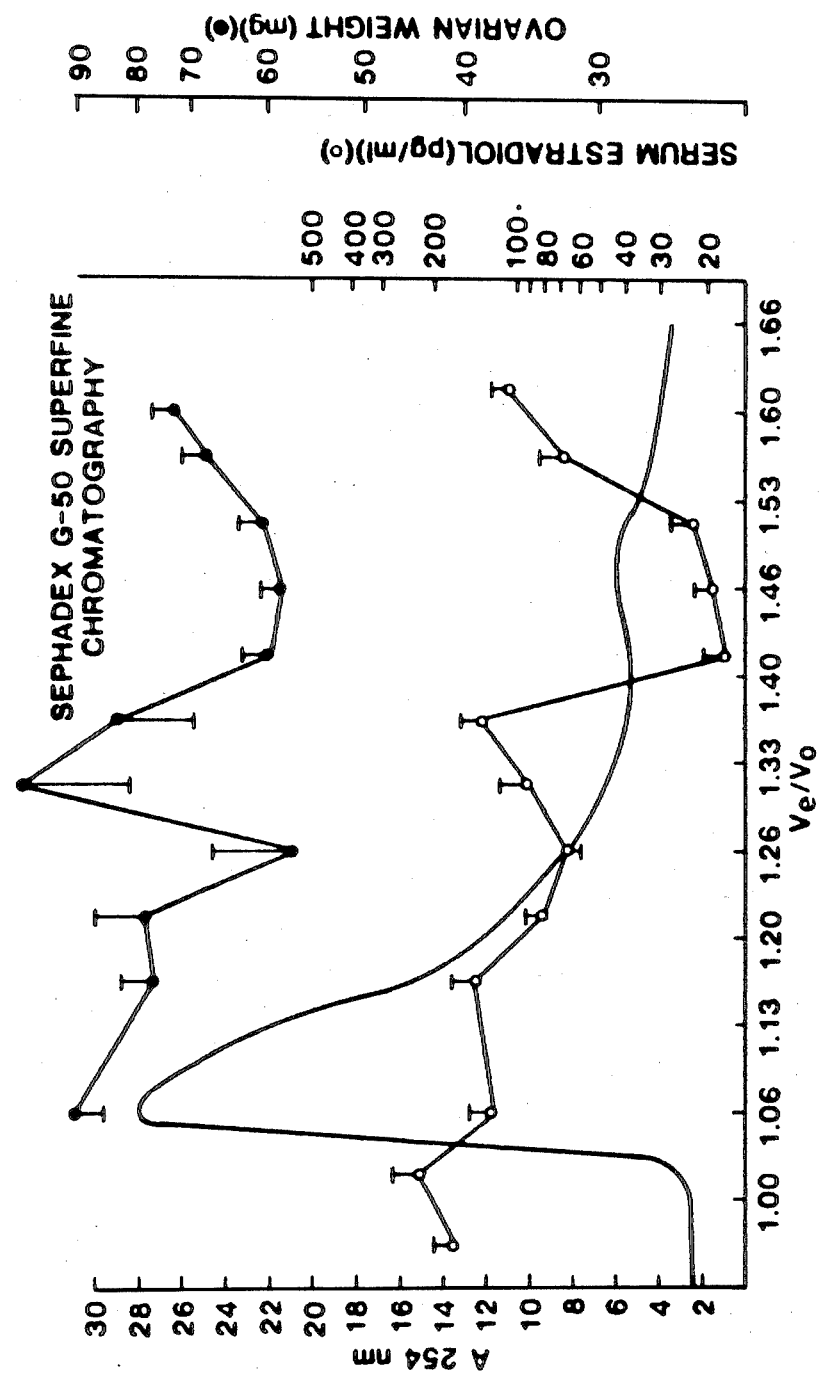
FIG. 2 shows the elution profile of a preovulatory patient's ovarian venous effluent after partial purification using Sephadex G-50 superfine chromatography with absorbance measured at 254 nm. The responses, by bioassay of hypophysectomized, twenty-three day old, DES-treated rat ovaries receiving hMG therapy to aliquots of the Sephadex G-50 fractions in terms of ovarian weight and serum $17\beta$-estradiol concentrations are overlayed. Fractions eluting with a $V_e/V_0$ of 1.42-1.55 actively inhibited both parameters.

FIG. 2 compares absorbency, at 254 nm, of the Sephadex G-50 fractions from a preovulatory ovarian venous sample of patient 1 to the bioassay results of the sample, as determined by rat ovarian weight and serum 17$\beta$-estradiol concentrations. An initial peak rose to 28 absorbency units, followed by a gradual downward slop, with the emergence of a smaller second peak ($V_e/V_o$=1.42–1.55). When these eluents were tested in the bioassays, the combined rat ovarian weights ranged from 57–100 mg, and rat serum 17$\beta$-estradiol levels ranged from 70–230 pg/ml throughout the initial fractions. Thereafter, fractions with a $V_e/V_o$ of 1.42–1.55 corresponded to an inhibition of hMG-induced ovarian stimulation in the bioassay, as evidenced by a decrease in ovarian weight (59$\pm$0.5 mg) and a significant ($P<0.01$, by paired t test) decrease in serum 17$\beta$-estradiol to levels less than 25 pg/ml. As a consequence, these fractions were pooled and processed for dose response activity. Peripheral and ovarian venous blood collected from the ovary contralateral to the site of ovulation in patient 1 demonstrated similar G-50 elution profiles (data not shown). However, when representative fractions were tested by bioassay, no reduction in ovarian weight or serum 17$\beta$-estradiol was found. Further, ovarian venous blood preparations from the anovulatory patients also failed to suppress the response of the ovaries to hMG stimulation. However, ovarian venous sera from the ovulatory ovary of patients 2 and 3 had a similar Sephadex G-50 elution profile. Fractions with a $V_e/V_o$ of 1.48–1.60 suppressed the response of rat ovarian weight (57.4$\pm$2.1 vs. 81.2$\pm$4.5 mg; $P<0.05$) and serum 17$\beta$-estradiol concentrations ( 25 vs. 68–120 pg/ml; $P<0.01$) to hMG stimulation. When active fractions from the G-50 eluents of patients 1–3 were heated or trypsin digested, they lost their ability to suppress ovarian weight or 17β-estradiol secretion in response to hMG stimulation.

Figure 3:
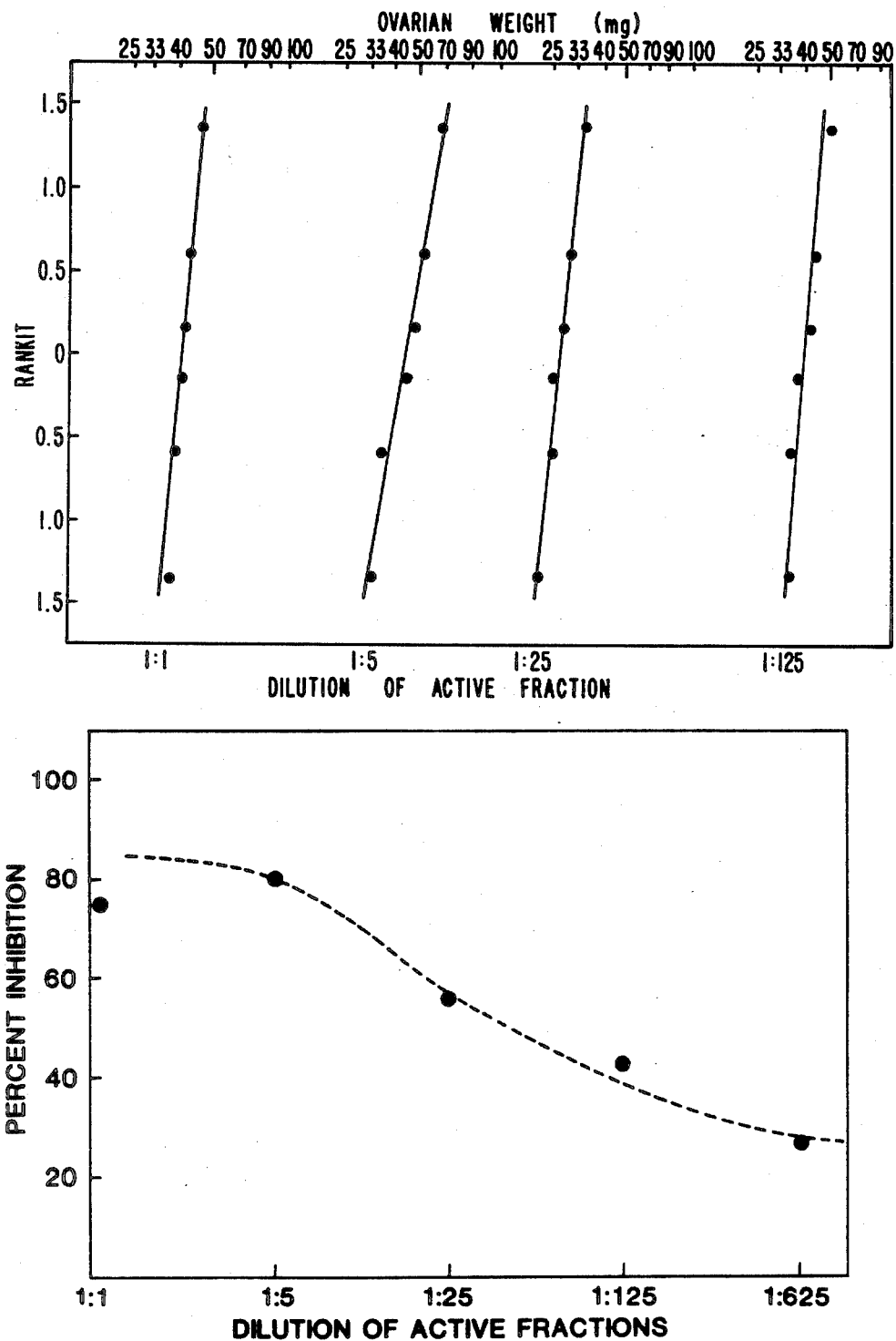
FIG. 3 shows the dose-response of active Sephadex G-50 fractions ($V_e/V_0 = 1.42$-1.55) in bioassay of hypophysectomized, twenty-three day-old, DES-treated rat ovaries receiving hMG treatment. *insert*, Rankit analysis to determine the central tendence for ovarian weight inhibition at each dose tested.

FIG. 3 depicts the dose-response curve of ovarian weight suppression in the DES-treated rat ovaries by active Sephadex G-50 fractions ($V_e/V_o = 1.42-1.55$) derived from patient 1. Analysis of the rat ovarian weight and serum (17β-estradiol) concentrations revealed a central tendency (insert: ovarian weights), the O-intercept of which displayed a linear dose-response pattern. When these same fractions were treated with heat or trypsin, no suppression of ovarian weight was present.

Figure 4:
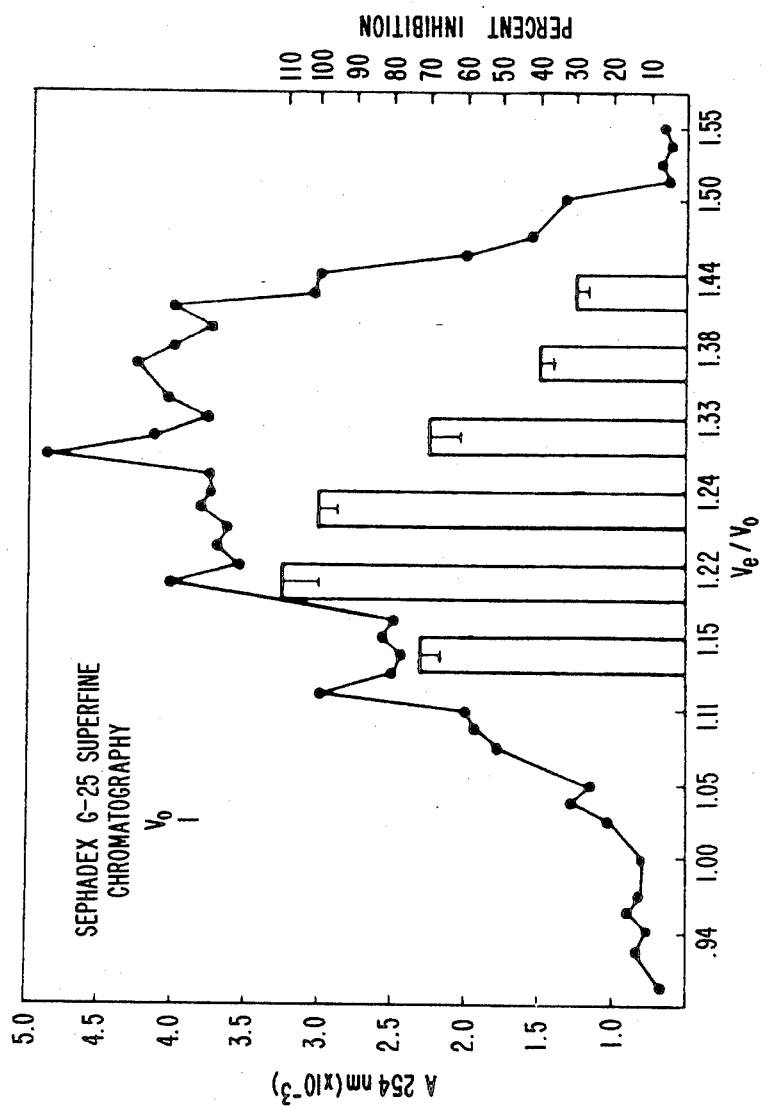
FIG. 4 shows the elution profile of Sephadex G-50 active fractions eluted from a Sephadex G-25 superfine column. Response is determined by the bioassay of hypophysectomized, twenty-three-day old, DES-treated rat ovaries receiving hMG therapy (ovarian weight) of these fractions. Note that fractions with a $V_e/V_o$ of 1.20-1.24 completely inhibited the rat ovarian weight response to hMG.

FIG. 4 depicts the Sephadex G-25 elution profile of the pooled active fractions from the Sephadex G-50 purification step. A generalized elevation in elution profile, as monitored by absorbency at 254 nm, occurred between $V_e/V_o$ 1.05-1.50. Representative fractions from this elution profile ($V_e/V_o = 1.20-1.24$) exhibited a complete inhibition (100%) of ovarian weight and 17β-estradiol (85%) responses to hMG stimulation.

The isoelectric point of active fractions eluted from the Sephadex G-50 column was estimated by ampholyte displacement chromatography. Pooled aliquots (1 ml) of active fractions were layered on a Polybuffer Exchanger 94 (25 ml; equilibrated to pH 7.4 with 0.025 M Imidazole HCl) column (0.6×30 cm). Fractions were eluted with Pharmalyte(TM) Polybuffer(TM) 74-HCl adjusted to pH 4.0 with HCl 1 N at 10 ml/h at 4° C. Fractions that eluted at a pH greater than 7.4 were collected and rechromatographed in the same Pharmalyte column reequilibrated to pH 9.4 with ethanolamine 0.025 M and eluted with Polybuffer 96 adjusted to pH 6.0 with 1 N KOH.

Figure 5:
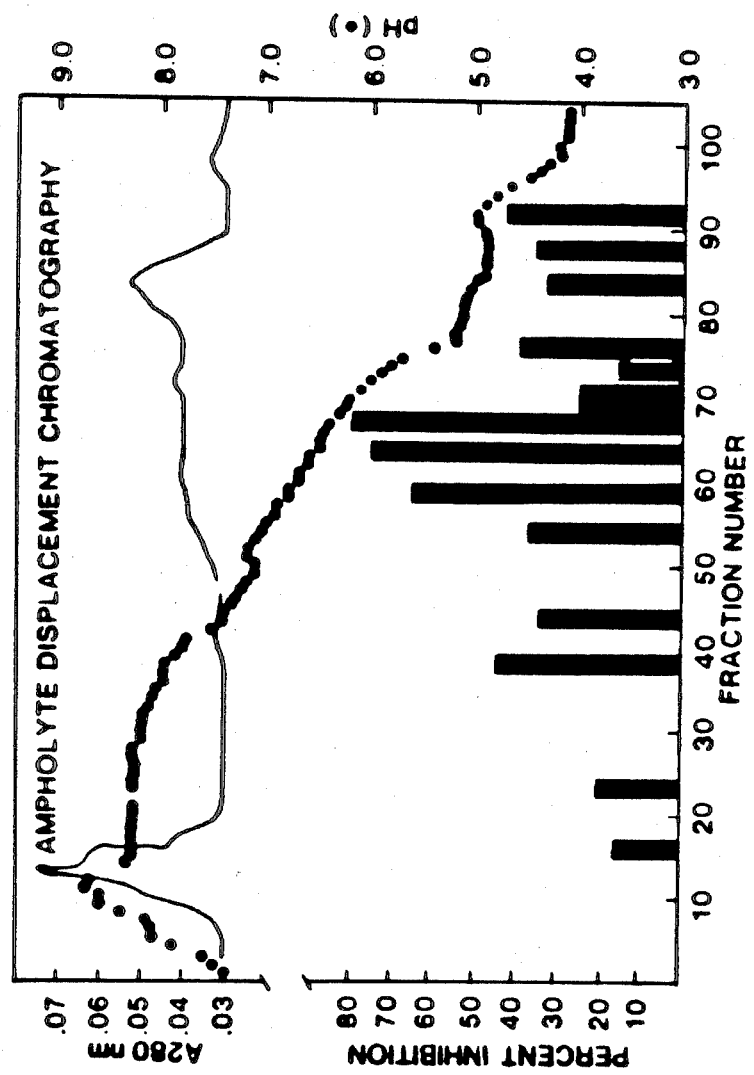
FIG. 5 shows a compilation of the active Sephadex G-25 fractions ($V_e/V_o = 1.20$-1.25) pooled and developed by ampholyte displacement chromatography. Fractions corresponding to a pH of 6.1-6.5 manifest inhibitory activity in excess of 50% tested in the bioassay with hypophysectomized, twenty-three-day-old, DES-treated rat ovaries receiving hMG therapy (ovarian weight). Ampholyte displacement chromatography of the fractions with follicle-inhibiting activity obtained on Sephadex G-25 gel filtration ($V_e/V_o = 1.20$-1.25).

FIG. 5 compiles the active Sephadex G-25 fractions ($V_e/V_o = 1.20-1.25$) pooled and developed by ampholyte displacement chromatograms from patient 1 for elution ranges pH 9-4. The bioassay results from ovarian weight and serum 17β-estradiol concentrations from representative fractions suggested that the isoelectric point of the active Sephadex G-50 eleuents from patient 1 were between pH 6.2-6.5.

Fractions corresponding to a pH of 6.1-6.5 manifest inhibitory activity in excess of 50% tested in the bioassay with hypophysectomized, twenty-three-day-old, DES-treated rat ovaries receiving hMG therapy (ovarian weight). Ampholyte displacement chromatography of the fractions with follicle-inhibiting activity obtained on Sephadex G-25 gel filtration ($V_e/V_o = 1.20-1.25$).

Figure 6:
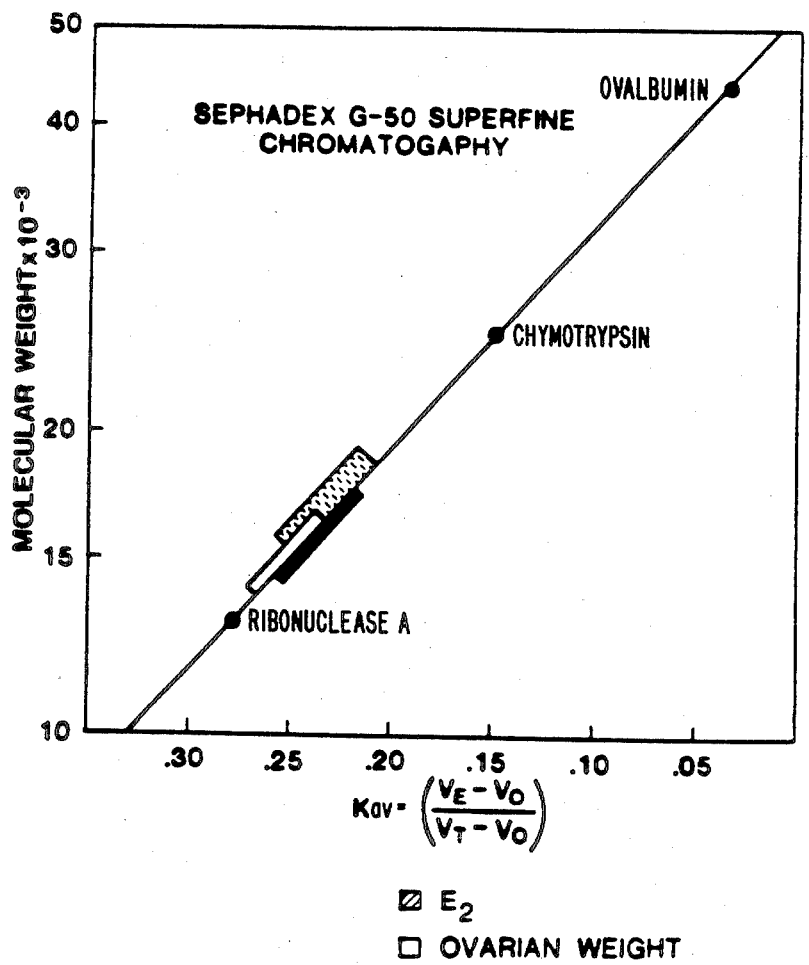
FIG. 6: $K_{av}$ of the active portion of preovulatory ovarian venous effluents from patients 1-3 eluted through a Sephadex G-50 superfine column calibrated with molecular weight standards. The molecular weights estimated in this manner were 14,000-16,500 for patient 1, (▢) 14,000-17,000 for 2 (■) and 16,000-18,000 for patient 3 (▨).

FIG. 6 depicts the $K_{av}$ values for the molecular weight standards and active Sephadex G-50 fractions from patients 1-3. Estimations of molecular weight ranged from 14,000-16,500 for patient 1, from 14,000-17,000 for patient 2, and from 16,000-18,000 for patient 3.

Thus, it is seen that at least one protein is secreted by the preovulatory ovary which suppresses the follicle response to gonadotropins. Specifically, a heat- and trypsin-labile substance secreted directly into the venous drainage from the ovary containing the dominant follicle which suppresses the follicular response to gonadotropins. That this protein is not secreted in large amounts by anovulatory ovaries was evidenced by the failure of the bioassay to detect inhibitory activity in the venous drainage of the contralateral ovary of patients 1-3 as well as the ovarian venous effluents from three anovulatory women. This potential intra- and/or interovarian regulator of folliculogenesis mediates dominance of the preovulatory follicle by an active process, such that after the selection of the dominant follicle, the gonadotropin responsivity of other follicles on the same and contralateral ovaries is suppressed.

EXAMPLE TWO

Identification of Follicular Regulatory Protein(s) in Pooled Human Follicular Fluid To evaluate the role of nonsteroidal, follicular fluid proteins in folliculogenesis, the 10-55% saturated ammonium sulfate fraction of pooled human follicular fluid was dialyzed against 0.025 M Tris/HCl(pH 7.5) using 10,000 molecular weight exclusion membranes, then passed through agarose immobilized textile dye. Activity was determined by test fraction inhibition of human menopausal gonadotropin (2 U human LH/FSH day) induced ovarian weightgain, and serum estradiol increase in hypophysectomized, diethylstilbesterol-treated, twenty-five-day-old female rats.

Specifically, human follicular fluid (hFF) was aspirated from regularly menstruating women (aged twenty-five to thirty-five years) undergoing ovarian hyperstimulation during participation in an in vitro fertilization protocol by treatment with clomiphene citrate (150 mg/day for five days, beginning three to eight days after onset of spontaneously occurring menses) and hCG (5000 IU forty-eight hours before aspiration). Sera were collected daily and estrogen concentrations were determined. When serum estrogen concentrations exceeded 800 pg/ml, patients underwent laparoscopy for aspiration of follicles in excess of 20 mm in diameter. The follicular aspirate was immediately centrifuged (800 x g), the granulosa cells were removed and the aspirate was then frozen (−57° C.). Follicular aspirates from twenty such patients were pooled and provided the hFF used throughout this study.

Pooled hFF was slowly thawed and fractionated by dropwise addition of an equal volume of saturated ammonium sulfate (SAS) during persistent agitation at 4° C. After a twelve hour incubation at 4° C., the precipitate was pelleted, the supernatant was discarded, and the pellet was resuspended (2:1, vol/vol) with 10% SAS. An additional twelve hours of agitation was followed by centrifugation at 3,000 x g thirty minutes. The resulting supernatant was dialyzed using 10,000 molecular weight exclusion dialysis membranes against three changes of 0.025 M Tris/HCl, pH 7.5, (buffer A) for sixteen hours. Insoluble material was removed from the retentate by centrifugation (3,000 x g for 30 minutes).

A series of agarose (triazine ring) immobilized textile dyes (Dye-Matrix Screening Kit, Amicon, Lexicton, Mass.) were prepared according to the manufacturer's instructions. Columns (9×32 mm, 2 ml bed volume) containing Matrix Gel Blue A (triozinyl dye Cibacron Blue 3GA), Red A (Procion Red HE3B), Blue B (Cibacron Brilliant Blue FBR-P), Orange A, or Green A were equilibrated with 20 mM Tris/HCl (pH 7.5), then charged with 0.5 ml aliquots of the dialyzed retentate. Unbound material was eluted with 10 ml buffer A. The bound protein was eluted with 1.5 M KCl in buffer A. Eluent fractions were dialyzed overnight against buffer A, and protein concentration determined.

Eluents containing active material (Orange A-bound fractions) were further separated (10 ml/h, 4° C.) on a Sephadex G-50 (superfine) column (1.6×50 cm, $V_O = 60$ ml, 5 ml/h, 4° C.) with buffer A. Elution profiles were determined using an ISCO absorbance meter at 254 nm. For estimation of molecular weight by gel filtration, the same Sephadex G-50 column used for purification (2.6×70 cm, $V_t=280$, $V_O=90$ ml) was equilibrated and developed with molecular weight standards ribonuclease-A, chymotrypsin, and ovalbumin in buffer A at 10 ml/h, 4° C. Fractions were then assessed for activity in the bioassay. $K_{av}$ for each standard and active fraction was calculated using $V_t=280$, $V_O=90$ ($K_{av}=V_e-V_O/V_t-V_O$).

Additional aliquots from the 10–55% SAS fraction of the hFF (10 ml) were passed through a Concanavalin A-linked Sepharose 4B (Con A) column which was washed with 5 vol of 0.5 M NaCl, 0.05 M Tris/HCl (pH 7.4), then further eluted with 2 M α-methyl-D-mannoside in buffer A at a flow rate of 20 ml/h. Both Con A-bound and -unbound fractions were assessed for activity in the bioassay. Chromatography fractions containing inhibitory activity were heated (56° C., 1 h) or trypsin digested (10 mg/100 ml) for three hours, and then retested for bioactivity.

Both Orange A-bound and 10-55% SAS hFF were further purified by isoelectric focusing using a Sephadex G-15 support matrix. The apparatus consisted of a 4×30 cm water-jacketed glass column containing a 2.5×20 cm G-15 Sephadex bed supported by a 2.5×8 cm Teflon elution plug under a 25-mm Millipore filter. The column was previously equilibrated with two-bed volumes of a solution containing carrier ampholytes (4% of pH 3–10 and 4% of pH 2–4) in 12.5% glycerol. Cytochrome C was used as an internal marker protein (pI=10.5). The fractions were then washed into the column with 20 ml ampholyte-glycerol solution. A second Millipore filter was placed on the top of the Sephadex bed. A 10-ml polyacrylamide solution of 14% acrylamide, 0.3% Bis, and 50 M 1 N,N,N',n'-tetramethylethylenediamine (polymerized by the addition of 0.1 ml of 10% ammonium persulfate) was then poured over the filter. Upon completion of polymerization (twenty minutes), the column was inverted, the Teflon plug was removed, and a second acrylamide plug was layered over the bottom filter. After polymerization of the bottom plug, the column was returned to its upright position and lowered into anode buffer containing 1% sulfuric acid. The remaining upper portion of the column was filled with 1% ethanolamine. The column was cooled by recirculating water at 1°–4° C. throughout the procedure. Isoelectric focusing was initated at 800 constant V (16 mA) and allowed to proceed to equilibrium as monitored by an eventual decline in the milliamperage to 2.5 mA (8–12 h). Thereafter, pooled column fractions (3 ml) were dialyzed against buffer A to remove ampholytes before bioassay.

Since an apparent isoelectric point was reproducibly determined in material isolated from the human ovarian vein blood by ampholyte displacement chromatograph in Example One, this procedure was employed with the 10–55% SAS-dialyzed hFF. Pooled aliquots (10 ml) were layered onto a Polybuffer Exchanger 94 adjusted to pH 7.4 with 0.025 M Imidazole buffer, ml/h, 4° C. The column was eluted with Polybuffer 74 adusted to pH 4.0 with 1N HCl. Fractions that eluted at a pH greater than 7.4 were collected and rechromatographed in the same Pharmalyte column re-equilibrated to pH 9.4 with ethanolamine 0.025 M, and eluted with Polybuffer 96(TM) adjusted to pH 6.0 with 1 N KOH.

The rats used in the bioassay were hypophysectomized and implanted as described in Example One, and serum estradiol-17β concentration was determined as described previously.

Control determinations (no injected test fractions) for unstimulated ovarian weight were 34.7±3.2 (SEM) mg/rat and for LH-FSH-stimulated were 192.0±30.5 mg/rat. Control levels of trunk serum estradiol were 12.5±0.7 pg/ml for unstimulated rats, and 118.5±21 pg/ml for LH-FSH-stimulated. Where indicated, 100% inhibition equals ovarian weight and/or serum estradiol concentration of mean unstimulated control values. Zero percent inhibition equals ovarian weight or serum estradiol concentration of LH-FSH-stimulated control rats. These results are similar to those which have been obtained with the previous application of this bioassay procedure in Example One. Tests of statistical significance were performed by Student's t test and Duncan's multiple range analysis.

Protein separation was performed using a Waters HPLC/ GPC Model 244 Liquid Chromatograph equipped with a 0.75×50 cm TSK 3000 SW gel exclusion column. A 100 ul aliquot of the dialyzed, Orange A-dye-matrix eluent was separated on each high performance liquid chromatographic (HPLC) run. The proteins were eluted from the TSK column using an isocratic gradient of 0.02 M PBS (pH 7.0) at a flow of 0.5 ml/min. The protein peaks were detected by absorbance at 280 nm with a Waters variable wavelength detector (Model M-450) and molecular weight estimates of the specific follicular fluid proteins were performed using highly purified molecular weight chromatography standards of ribonuc-lease-A, chymotrypsin, ovalbumin, and bovine serum albumin (BSA).

Table 1 summarizes the results of Dye-Ligand matrix chromatography of the 10–55% SAS-dialyzed hFF fraction. Although Orange A bound only 17% of the charged protein, 1.5 M KCl eluted bioactive material that contained the greatest inhibition of the hMG-induced rat ovarian weight gain (89±6.8% SEM; $P<0.05$) when compared to the other Dye-Ligand eluents.

Figure 7:
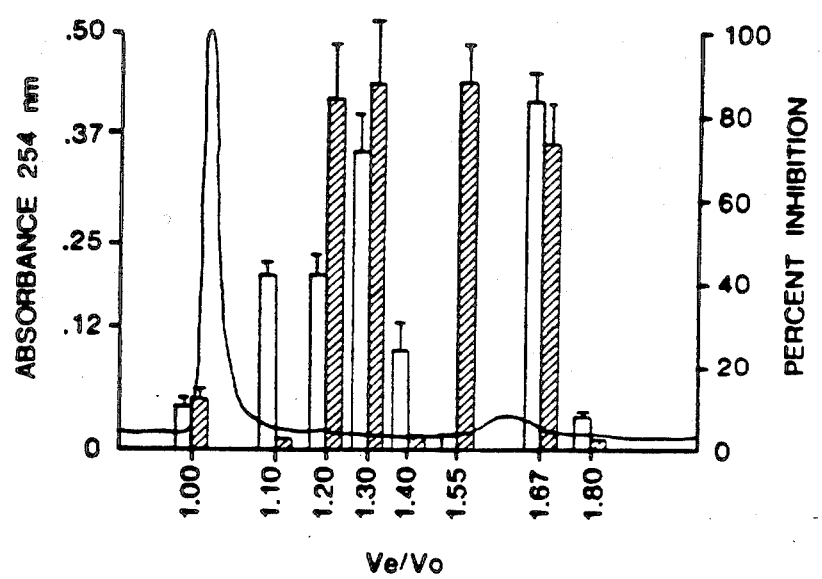
FIG. 7: shows an elution profile of the 10-55% SAS cut, dialyzed (>10,000 molecular weight), and developed through Orange A Dye-Matrix (1.5 M KCl), passed through Sephadex G-50. Fractions (2 ml) were tested in the LH-FSH-stimulated hypophysectomized, immature, DES-treated rat for inhibition of ovarian weight, and serum estradiol concentration (mean±SEM). Fractions with molecular weight corresponding to 12,000-15,000 and 22,000-25,000 contained inhibitory activity.

FIG. 7 depicts the chromatographic elution profile of hFF developed through Sephadex G-50 at 254 nm after SAS 10–55% cut, dialysis (>10,000 molecular weight), and elution of Orange A-bound material with 1.5 M KCl. Fractions (2 ml) were tested in the LH-FSH-stimulated hypophysectomized, immature, DES-treated rat for inhibition of ovarian weight, and serum estradiol concentration (mean±SEM). An initial peak in absorbance can be seen at $V_e-V_O$ ratio of 1.0–1.1, which after descending, reaches a gradual ascending second plateau ($V_e-V_O$ of 1.58–1.68). Biological activity was determined as inhibition of ovarian weight and trunk serum estradiol levels. The same column was then equilibrated with molecular weight standards and developed with buffer A, allowing for molecular weight estimation ($K_{av}=\log V_e-V_O/V_t-V_O$) for fractions containing inhibitory activity. Molecular weight of eluents containing inhibitory activity was estimated to be 13,000–15,000 and 22,000–25,000.

Figure 8:
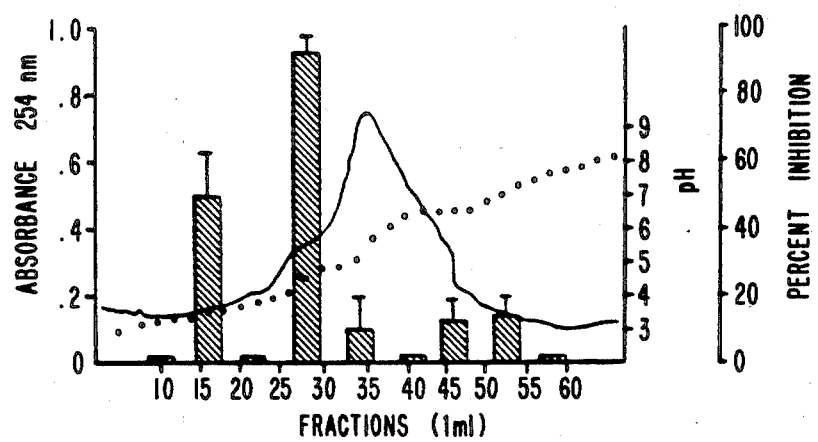
FIG. 8. Isoelectric focusing chromatogram of pooled human follicle fluid after SAS precipitation (10-55%), dialysis (>10,000 molecular weight) and Orange A Dye-Matrix chromatography (1.5 M KCl eluent). Fractions corresponding to an isoelectric point of pH 3.5-4.5 contained inhibitory activity of rat ovarian weight and trunk estradiol (not shown) in the bioassay after gonadotropin challenge.
Figure 9:
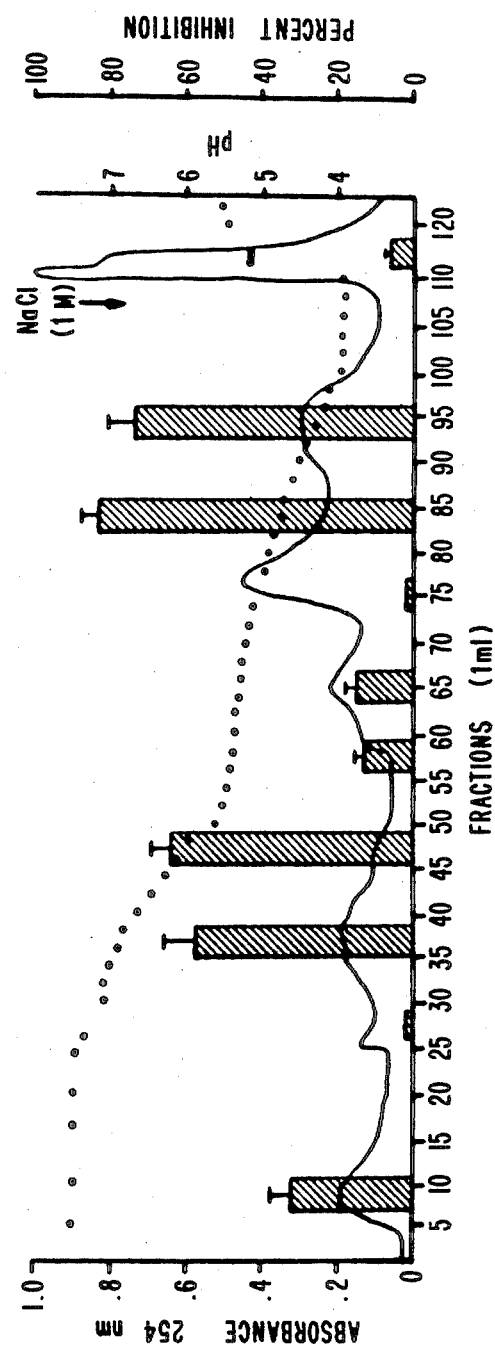
FIG. 9: Ampholyte displacement chromatogram of pooled hFF after SAS precipitation (10-55%), dialysis (>10,000 molecular weight) and Orange A Dye-Matrix chromatography (1.5 M KCl eluent). Fractions corresponding to an isoelectric point of pH 3.5-4.5 and pH 6.5-7.0 contained inhibition of rat ovarian weight (mean±SEM) in the bioassay after gonadotropin challenge.

Eluents from the isolectric focusing of hFF after SAS (10–55%), dialysis (>10,000 molecular weight), and Orange A dye matrix chromatrography (1.5 M KCl eluate) (FIG. 8) were evaluated for activity in the bioassay. Only fractions in the pH range of 3.5–4.5 contained clear inhibition of ovarian weight and trunk 17B-estradiol levels (not shown). When isoelectric point determination was performed using ampholyte displacement chromatography (FIG. 9), inhibition of rat ovarian weight was found in the pH range 3.5–4.5. In addition, a second area of inhibition in the bioassay was noted (pH 6.5–7.0) that was not present after isolectric focusing.

Figure 10:
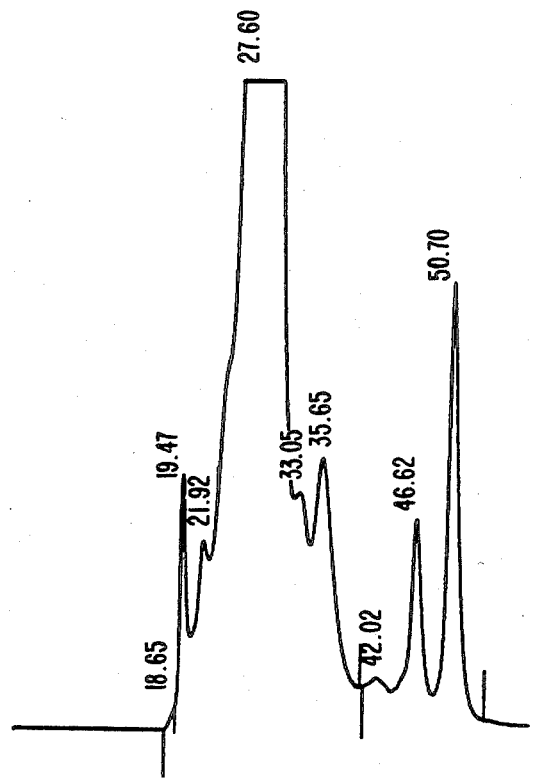
FIG. 10: Representative high performance liquid chromatogram of the Orange A-bound fraction of the 10-55% SAS hFF. Fractional retenton times corresponded to the following molecular weight ranges: 21.0-23.0 minutes; 100,000; 23.0-25.0 minutes, 100,000; 25.0-28.5 minutes, 70,000-100,000; 28.5-32.2 minutes, 40,000-70,000; 32.2-34.0 minutes, 30,000-40,000; 34.0-40.0 minutes, 18,000-30,000; 40.0-45.0 minutes 5,500-18,000; 45.0-49.0 minutes, 2,500-5,500; 49.0-53.0 minutes, <2,500.

FIG. 10 depicts the HPLC elution profile of the Orange A-bound extracted hFF material. The HPLC eluent was divided into ten fractions based on peak absorbances [0: 18.5–21.0 minutes (void volume); 1: 21.0–23.0 minutes; 2: 23.0–25.0 minutes; 3: 25.0–28.5 minutes; 4: 28.5–32.2 minutes; 5: 32.2–34.0 minutes; 6: 34.0–40.0 minutes; 7: 40.0–45.0 minutes; 8: 49.0 minutes; 9: 49.0–53.0 minutes]. These fractions corresponded to the following molecular weight ranges: 1, 100,000; 2, 100,000; 3, 70,000–100,000; 7: 5,500–18,000; 8: 2,500–5,500; 9, 2,500. The retention times of peak absorbances after HPLC elution, when correlated to molecular weight standards, were highly reproducible (13 runs).

Figure 11:
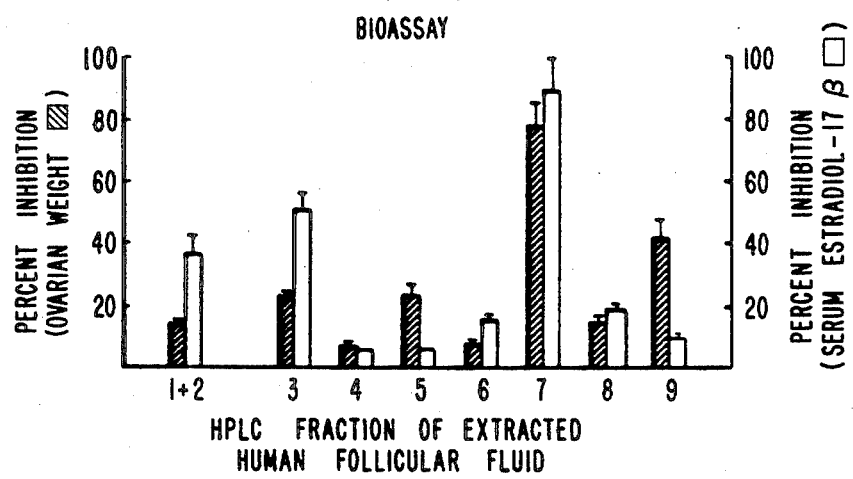
FIG. 11: Bioassay results of HPLC fraction of Orange A bound hFF. Inhibition of LH-FSH-induced ovarian weight augmentation in immature, hypophysectomized, DES-treated rats (mean±SEM) was evident in those treated with the 5,500-18,000 molecular weight fractions (no. 7, n=3 rats at each level).

When HPLC fractions were tested in the bioassay (see FIG. 11), inhibition of ovarian weight gain and serum estradiol elevation were evident in rats injected with the 5,500–18,000 molecular weight fraction [78±8% (SEM) and 89±10%, respectively ($P<0.01$)] as compared to the other fractions.

In Example One, there is described a protein, in the venous drainage of the human ovary which contains the preovulatory follicle, which suppresses the follicular response to gonadotropins. That this protein was not secreted in large amounts by anovulatory ovaries was evidenced by failure of the bioassay to detect inhibitory activity in the venous drainage of the contralateral ovary in ovulatory patients as well as both ovarian vein effluents from anovulatory women. In the present example, a comparable isolation procedure has shown a similar biological activity in human follicular fluid (hFF). The rat bioassay employed to identify material in hFF which inhibits LH-FSH-mediated follicular stimulation was the same as that reported for human ovarian vein blood extracts. Follicular inhibitory activity in hFF had a molecular weight, determined by HPLC size exclusion chromatography (10,000–18,000) that is similar to that of follicular inhibitory activity recovered from human ovarian vein serum (14–17,000). The indicated isoelectric point for inhibitory activity in human ovarian vein extract, as determined by chromatofocusing (pH 5.8–6.4), is similar to the hFF extract reported here.

The follicular inhibitory substance reported here was derived from follicular aspirates of women during spontaneous ovarian cycles whose follicles were hyperstimulated by clomiphene and hCG therapy. Consequently, no conclusion can be drawn regarding this material in normally developing follicles. However, since a similar activity has been identified in the ovarian vein serum draining the spontaneous preovulatory ovary (Example One) these data indicate this inhibitory protein to be a product of the dominant follicle itself.

EXAMPLE THREE

Identification of Follicular Regulatory Protein(s) in Human Granulosa Cell Secretions Follicular fluid was aspirated from regularly menstruating women (twenty-five to thirty-five years old), undergoing clomiphene citrate (150 mg/day for five days, beginning three-eight days after the onset of spontaneously occurring menses) and hCG (4000 IU, 36 hours before aspiration) therapy during participation in an in vitro fertilization protocol. Serum was collected daily, and estrogen concentrations were determined. When serum estrogen concentrations exceeded 800–1000 pg/ml, patients underwent laparoscopy for aspiration of follicles in excess of 20 mm in diameter. Follicular aspirates were immediately centrifuged (800 x g), granulosa cells were removed for culture, and the supernatant was frozen ($-57°$ C.). Follicular aspirates from seven patients were evaluated.

The aspirated follicular fluid volume, number of viable granulosa cells, and follicular fluid steriod concentrations from the largest follicle recovered from the seven patients are depicted in Table 2. All of the antral fluids contained high concentrations of progesterone (7–12 ug/ml), indicating premature luteinizations of the follicles (30–32) as a result of the clomiphene/hCG therapy. Approximately 100,000 viable granulosa cells were obtained from each follicle.

Individual hFF samples were slowly thawed and fractionated by dropwise addition of an equal volume of saturated ammonium sulfate during persistent agitation at 4° C. After a twelve hour incubation at 4° C., the precipitate was recovered by centrifugation and resuspended (2:1, vol/vol) in 10% ammonium sulfate. An additional twelve hours of mixing was followed by centrifugation at 3,000 x g for thirty minutes. The resulting supernatant was dialyzed (10,000 molecular weight exclusion membranes) against phosphate-buffered saline (PBS) (0,025 M; H 6.8) for sixteen hours at 4° C. and then lyophilized. The retentate (500 mg in 0.5 ml aliquots) was passed through a column (9×32 mm; bed volume, 2 ml) containing agarose-immobilized Orange A (Dye matrix, Amicon), which had been equilibrated with 20 mM Tris-HCl, pH 7.5. Unbound material was eluted with 10 ml 20 mM Tris-HCl, pH 7.5 and bound material was eluted with 10 ml 1.5 M KCl in 20 mM Tris-HCl pH 7.5. Bound eluent fractions were dialyzed overnight against PBS or distilled water. Protein concentrations were determined by the method of Lowry et al., *J. Biol. Chem.* 143:265.

Rats were prepared for bioassay as described in the previous examples.

Results of control determinations (no injected test fractions) were 34.8±3.2 mg/rat for unstimulated ovarian weight and 122.0±13.5 mg/rat for FSH-stimulated ovarian weight. Control levels of trunk serum estradiol were 12.5±0.7 pg/ml for unstimulated and 118.5±21 pg/ml for LH/FSH stimulated. Where indicated, 100% inhibition equals the ovarian weight and/or serum estradiol concentration of mean unstimulated control values. Zero percent inhibition equals the ovarian weight or serum estradiol concentration of LH/FSH-stimulated control rats. These results are similar to those obtained during the previous examples. Tests of statistical significance were performed by Student's t test and Duncan's multiple range analysis.

Figure 12:
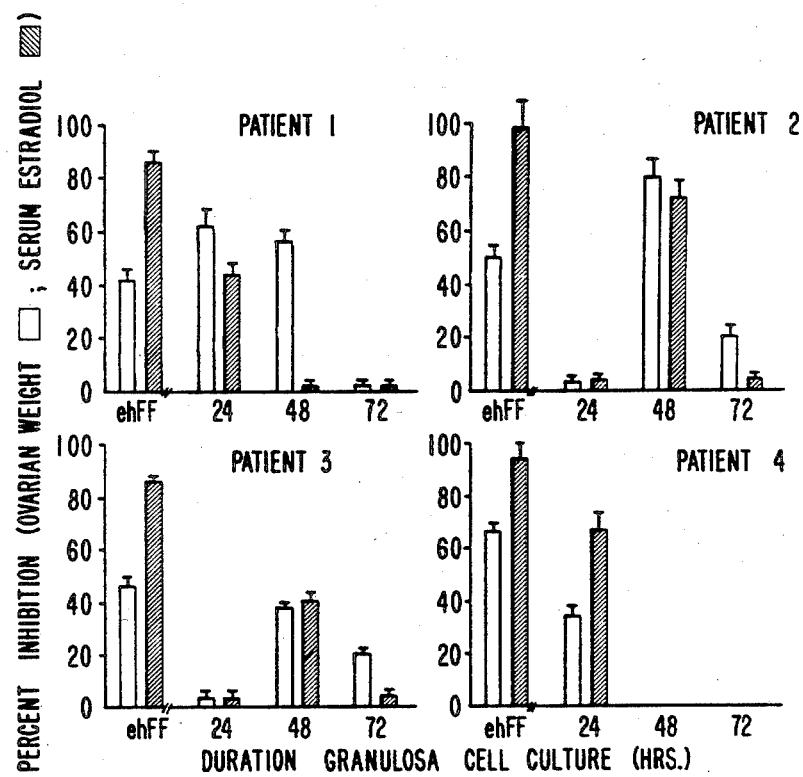
FIG. 12: Effect of ehFF and respective granulosa cell culture media (twenty-four, forty-eight and seventy-two hours) on the inhibitiln of LH/FSH (2 IU)-stimulated immature, hypophysectomized, DES-treated rat ovarian weight augmentation and serum estradiol secretion (2 ml/rat). Each value represents the mean±SE of three rats.

FIG. 12 depicts the effect of extracted follicular fluid (ehFF) and respective granulosa cell culture media (24, 48, and 72 hours) on the inhibition of LH/FSH (2 IU)-stimulated rat ovarian weight augmentation and serum estradiol secretion (2 ml/rat). Each value represents the mean±SEM of three rats.

All four follicular fluid extracts (ehFF) contained inhibitory activity, as evidenced by inhibition of both rat ovarian weight (40–65%) and trunk serum estradiol concentrations (85–100%). Bioassay of culture media from the respective granulosa cell cultures collected twenty-four, forty-eight and seventy-two hours after plating indicated that inhibitory activity was present during the first forty-eight hours of incubation. Variability in the initial twenty-four hour determination of patients 2 and 3 may relate to initial plating efficiency. Importantly, all bioassay determinations were made after complete medium changes each twenty-four hours. No inhibitory activity was noted after seventy-two hours of culture.

Figure 13:
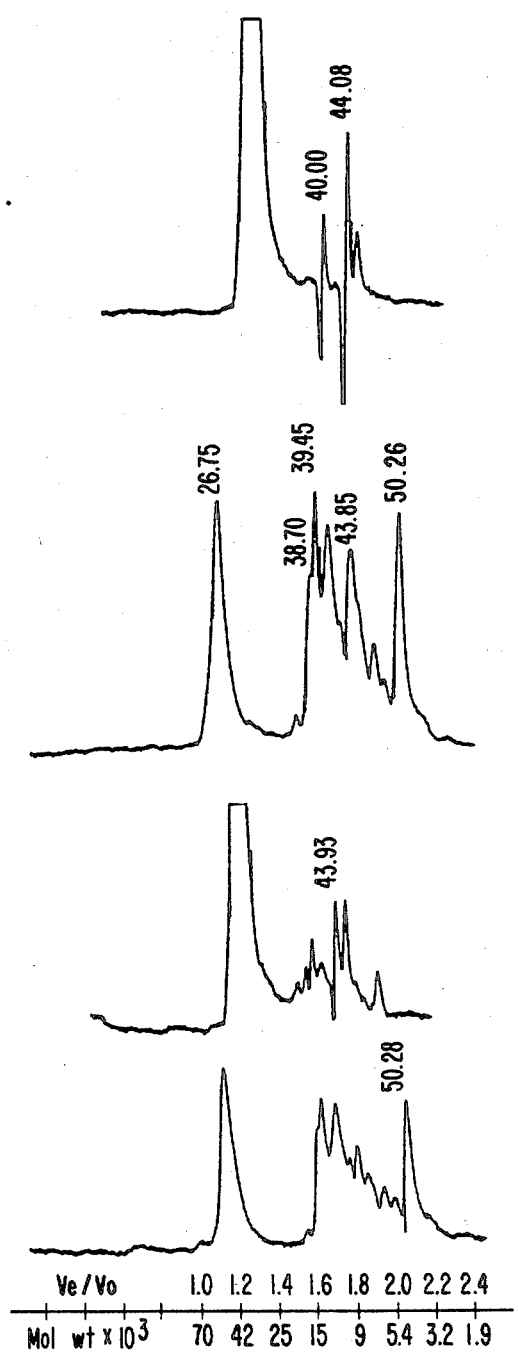
FIG. 13: HPLC elution profiles of ehFF from patients 1-4 developed through gel exclusion columns. Inhibitory activity, as determined by suppression of LH/FSH enhancement of hypophysectomized, immature, DES-treated rat ovarian weight augmentation and estradiol secretion, was continued in all four extracted FF samples (See FIG. 12).

FIG. 13 depicts the HPLC elution profiles of ehFF developed through the I-125 gel exclusion columns from patients 1-4. As can be seen, absorbance at 280 nm was present in all extractions within the molecular weight range of 12,000-17,000 similar to the molecular weight range of biological activity extracted from ovarian venous serum (Example One) and pooled hFF (Example Two), as determined by Sephadex chromatography.

Figure 14:
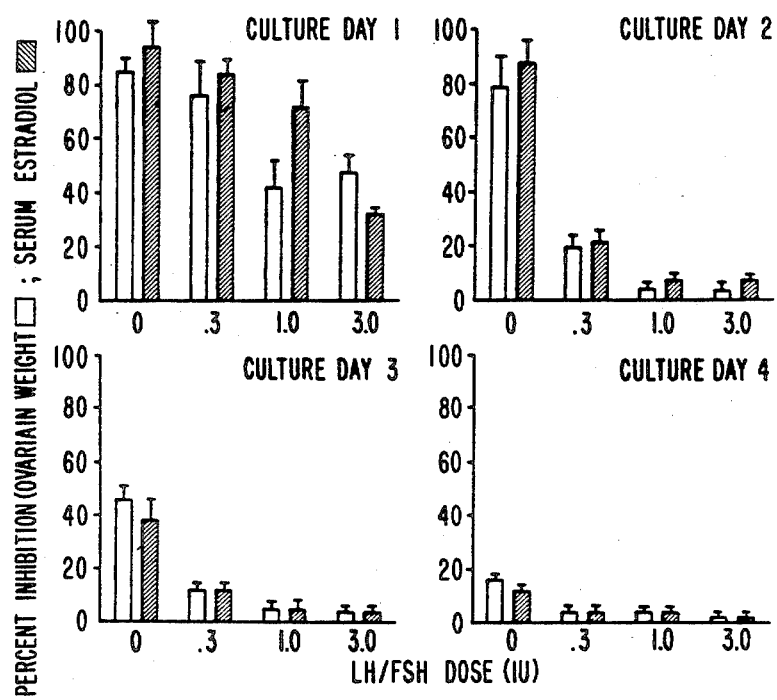
FIG. 14: Effect of granulsa cell culture medium (2 ml/rat) on the inibition of ovarian weight augmentation and serum estradiol responses to LH/FSH stimulation in the immature, hypophysectomized, DES-treated rat. Each value represents the mean±SE of nine rats. Granulosa cells were aspirated from three patients (no. 5-7) who underwent clomiphene (150 mg/day, menstrual cycle days 3-7) and ACG (4000 IU, 36 hours before aspiration) treatment.

FIG. 14 depicts the compiled (mean±SE) bioassay results of culture media derived from granulosa cell cultures of patients 5, 6, and 7. All media tested without gonadotropins added to the culture contained inhibitory activity of both ovarian weight and trunk serum estradiol concentrations exceeding 75% throughout the first two days of culture. Thereafter (days 3 and 4), the inhibitory activity of media from unstimulated cultures declined (43% and 37%, and 18% and 12% for ovarian weight and serum estradiol levels, respectively). After coincubation of the granulosa cells with varying doses of LH/FSH (0.3, 1.0 and 3.0 U), inhibitory activity, as determined in the HIFR-hMG bioassay, was markedly suppressed in all cultures after the first twenty-four hours (>20%).

Figure 15:
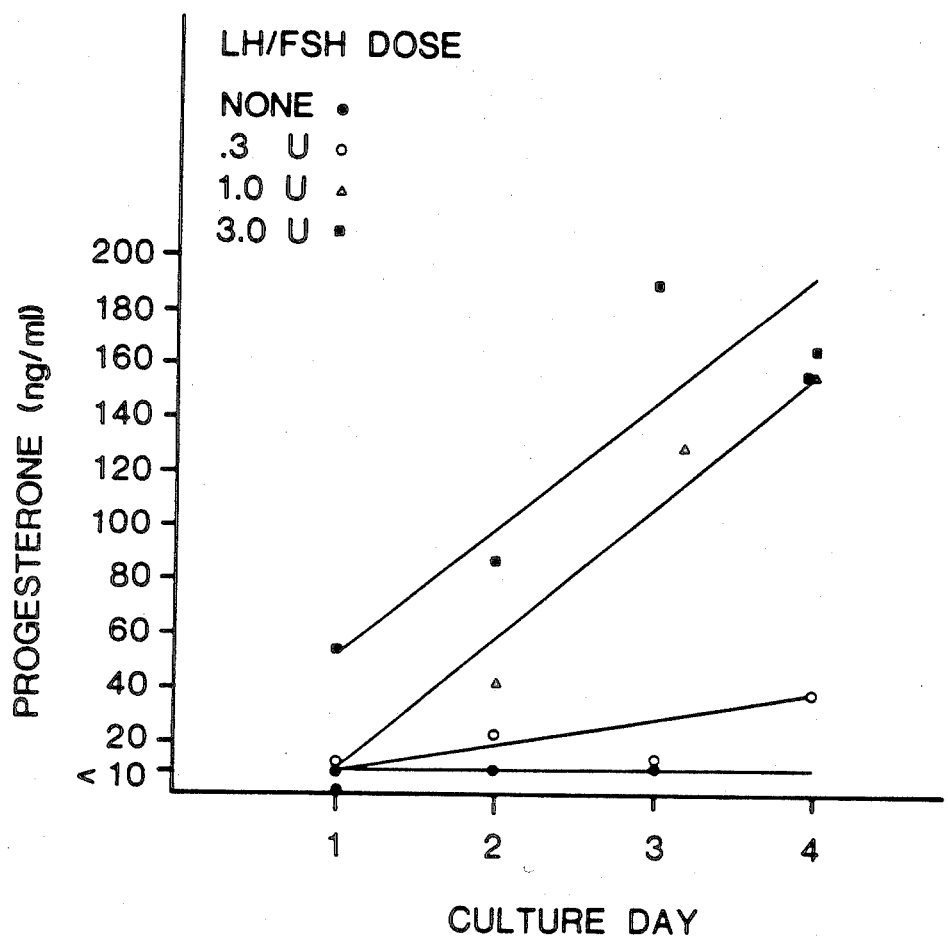
FIG. 15: Correlation of granulosa cell culture medium progesterone concentrations from patients 5-7 (see FIG. 14) with the duration of culture. The unstimulated cultures (no added LH/FSH) contained the least progesterone throughout the four days (less than 10 ng/ml) and continued to contain inhibitory activity (see FIG. 14). As LH/FSH was added to the cultures in increasing amounts, the progesterone concentrations rose in a dose-and time-dependent pattern, while bioassay of inhibitory activity declined to the limits of bioassay detectability (see FIG. 14).

When progesterone concentrations were determined for these culture media (FIG. 15), an inverse correlation between inhibitory activity in the bioassay and culture medium progesterone concentrations was apparent. The unstimulated cultures (no added LH/FSH) had the least progesterone throughout the four days of culture (<10 ng/ml), but contained inhibitory activity (FIG. 14), albeit in decreasing amounts as culture duration continued. However, after LH/FSH was added to the granulosa cell cultures in increasing amounts, the progesteone concentrations rose in a dose-and time-dependent pattern, while bioassay inhibitory activity declined to essentially the limits of bioassay detectability (FIG. 14).

High performance liquid chromatography

The high performance liquid chromatographic (HPLC) separation of follicular fluid steroids was performed. Steroid chromatographic standards were prepared in MeOH, and final dilutions made with the eluting solvent. Retention time and peak area for each steroid were determined by multiple injections at various concentrations for each steroid singly and pooled with other standards, using the Waters (Waters Associates, Milford, Mass.) Automatic Sample Processor (WISP-710-B). An HPLC/ GPC model 244 liquid chromatograph was employed for all separations. Elutions were performed on a $\mu$-Bondapak C-18 reverse phase column (3.9 mm; 10×30 cm; Waters No. 27324) using acetonitrile-water at 35:65 or 40:60 (vol/vol) and a flow rate of 3 ml/minute. Steroids were detected using a Waters M-450 variable wavelength detector at either 206 or 254 nm, and retention time and integrated peak area were calculated using a Waters No. 730 Data Module. Solvents were filtered through a Millipore filter (0.45 m m); before use and were degassed by ultrasonification for 7 minutes/liter. All organic solvents were HPLC grade, and deionized, double glass-distilled water was employed throughout.

Protein separation was performed using the same Waters HPLC/GPC Model 244 liquid chromatograph equipped with two Waters I-125 gel exclusion columns connected in series. A 10-$\mu$l aliquot of the dialyzed, Orange A dye matrix-bound eluent was separated on each HPLC run. The proteins were eluted from the I-125 columns using an isocratic gradient of 0.02 M PBS, pH 7.0, at a flow of 0.5 ml/minute (800 psi). The protein peaks were detected at 280 nm, and molecular weight estimates of the specific follicular fluid proteins were performed using highly purified molecular weight chromatography standards of ribonuclease-A, chymotrypsin, ovalbumin, and BSA.

Granulosa cells were cultured for up to four days in twenty-four hour intervals using 35×10-mm tissue culture dishes and 2 ml medium 199 containing 25 mM Hepes supplemented with 100 U/ml penicillin, 100 $\mu$g streptomycin sulfate, and 15% fetal calf serum (medium A). Cultures were maintained in a humidified, 95% air-5% $CO_2$ incubator at 37° C. After each twenty-four hour incubation period, spent medium was collected and stored frozen at $-20°$ C. until bioassay was performed. Where indicated, human menopausal gonadotropin (FSH-LH,1:1) was added to specific cultures at the time of complete medium change. At the end of each twenty-four hour incubation period, spent medium was collected for bioassay, and 2 ml fresh medium were added. The final cell pellets were dispersed in medium A, and aliquots (0.5 ml) the cell suspension were diluted with 0.05 ml trypan blue for quantitation of viable cells in a hemocytometer. Initial plating density was $0.5 \times 10^5$ granulosa cells/plate.

Granulosa cells were isolated from rat ovaries and were collected by centrifugation at 800 x g at 4° C. for ten minutes. FSH binding was determined using a modification of known techniques. Rat FSH, provided by the National Pituitary Agency, was labeled by the chloramine-T procedure. Cells were resuspended in appropriate volumes of PBS-01% gelatin (PBS-gel), pH 7.0. All assays were run with three concentration of labeled hormone (100 $\mu$l ), buffer (PBS-0.1% gel; 100 $\mu$l) and 100 $\mu$l cells. Reactions were initiated by the addition of granulosa cells and were carried out for four hours at 25° C. Reactions were terminated by adding 1 ml cold PBS, followed by centrifugation at 30,000 x g for ten minutes. The supernatant was carefully aspirated, and the pellet was rewashed with 1 ml PBS. The final pellet was counted in a $\gamma$-counter. Specific binding was calculated as the difference between binding in the presence (nonspecific) and absence (total) of an excess of unlabeled hormone.

Figure 16:
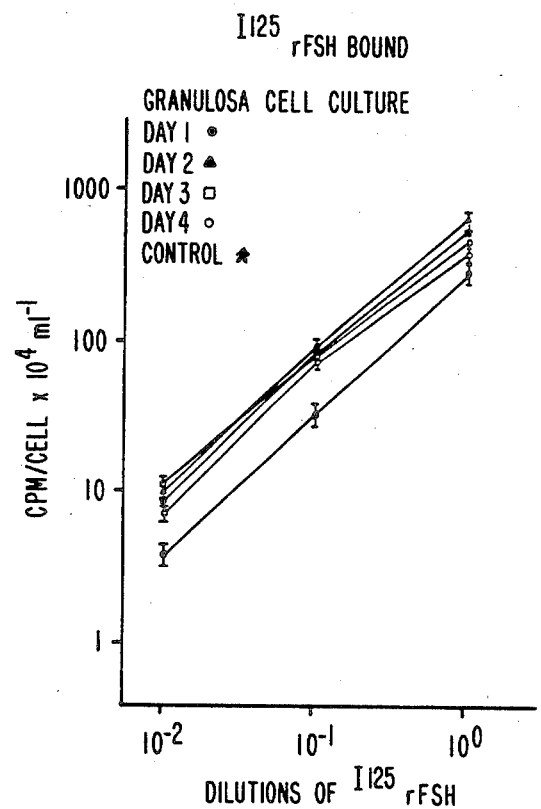
FIG. 16: Binding of FSH to rat granulosa cells collected from the HIFR-hMG bioassay of non-LH/FSH-stimulated human granulosa cell culture medium (see FIG. 14). Specific binding of rat FSH (rFSH) to granulosa cells was determined by incubating three concentrations of labeled rFSH in the presence and absence of excess unlabeled rFSH.

FIG. 16 depicts the FSH binding studies performed on the granulosa cells removed from the HIFR-hMG-treated rat ovaries used in the bioassay experiments shown in FIG. 12. Specific binding of rat FSH (rFSH) to granulosa cells was determined by incubating three concentrations of labeled rFSH in the presence and absence of excess unlabeled rFSH. Rat granulosa cell specific FSH binding was similar whether the rat received injections of spent medium from human granulosa cell cultures or saline. However, a marked difference in the ovarian weight and trunk serum estradiol concentrations of these rats was present (FIG. 12).

Replicate 0.1-ml portions of each rat granulosa cell suspension were pipetted into 12×75-mm polystyrene tubes. Androstenedione, the referent aromatase substrate, was added in 0.1 ml medium A (final concentration, $1.0 \times 10^{-7}$ M). All incubations were performed in triplicate for three hours at °37 C in a shaking water bath (120 cycles/minute). The reaction was stopped by transferring the tubes to an iced water bath before centrifugation for five minutes at 1000 x g. The supernatants were decanted and stored at −20° C. until measurements of estradiol and estrone were performed. Control incubations (no androstenedione added) were processed in the same way. Blank estrogen values obtained for the controls were subtracted from the corresponding values for incubations in the presence of androstenedione. Aromatase activity was expressed as estrogen production (nanograms per viable granulosa cell).

Figure 17:
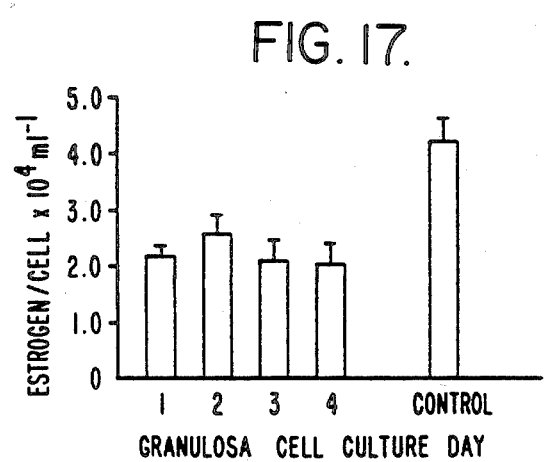
FIG. 17: Aromatase activity of rat granulosa cells derived from the HIFR-hMG bioassay of human granulosa cell culture medium (see FIG. 14, non-LH/FSH-stimulated cultures). Control determinations were performed on rat granulosa cells collected from HIFR-hMG-treated rats which did not receive culture medium injections. Inhibition of relative estrogen production by rat granulosa cells in the presence of $10^{-7}$ M androstenedine was seen throughout all four days of human granulosa cell culture medium treatment.

Rat granulosa cell aromatase activity is shown in FIG. 17 and was markedly inhibited ($P < 0.01$) by treatment with spent media from all four days of culture ($2.4 \pm 0.4$, $2.9 \pm 0.7$, $2.4 \pm 0.4$, and $2.1 \pm 0.2$ pg estrogen/10,000 viable cells/ml, respectively, compared to saline control $4.6 \pm 0.2$ pg estrogen/10,000 viable cells/ml. Control determinations were performed on rat granulosa cells collected from HIFR-hMG-treated rats which did not receive culture medium injections. Inhibition of relative estrogen production by rat granulosa cells in the presence of $10^{-7}$ M androstenedione was seen throughout all four days of human granulosa cell culture medium treatment. Taken together, these data indicate that although no marked inhibition of rat granulosa cell FSH binding was induced by the human grandulosa cell culture medium, a clear disruption of aromatase activity occurred, which may account for the decreased rat ovarian weight and serum estradiol concentrations.

Using the same purification techniques and bioassay described in Examples One and Two, a similar protein or proteins have been identified in the culture media derived from the granulosa cells of human follicles. This data indicates that human granulosa cells secrete a protein that inhibits follicular response to gonadotropins.

All of the antral fluid's steroid concentrations suggested premature luteinization. After extraction, all seven follicular fluids contained inhibitory activity, as evidenced by reduction of both rat ovarian weight (45-85%) and trunk serum estradiol concentrations (85-100%) in the HIFR-hMG bioassay. Bioassay of these follicles' granulosa cell culture media indicated inhibitory activity present during the first forty-eight hours, while no inhibitory activity was noted after seventy-two hours of culture. Spent culture media derived from granulosa cells cultured without additional gonadotropins contained inhibitory activity in the HIFR-hMG bioassay throughout the first two days in vitro. Thereafter (days 3 and 4), inhibitory activity of media from unstimulated cultures declined. After coincubation of the granulosa cells with varying doses of LH/FSH, inhibitory activity was markedly suppressed even after the first twenty-four hours. An inverse correlation was apparent between inhibitory activity in the bioassay and the culture medium progesterone level. Although FSH binding of granulosa cells derived from rats used in the HIFR-hMG bioassay was similar with or without injection of test fractions, their aromatase activity was markedly inhibited by treatment with human granulosa cell culture medium. These data indicate that although no marked inhibition in rat granulosa cell FSH binding was induced by the human granulosa cell culture medium, a clear disruption of aromatase activity occurred, which accounts for the decreased rat ovarian weight and serum estradiol concentrations found in the bioassay. Disruption of gonadotropin-mediated aromatase induction by an intrafollicular protein may, in part, modulate the local balance between C-19 steroid aromatase and 5-α-reductase enzymic activities in individual follicles.

A variety of nonsteroidal regulators of ovarian function have been identified in a variety of species, including oocyte maturation inhibitor, luteinizing inhibitor, folliculostatin or inhibin, and FSH binding inhibitor. The biophysical characteristics of the follicular inhibitor described here are different from such substances. This inhibitory material elutes through gel exclusion chromatography with a molecular weight of 12,000-17,000, binds to Orange A dye matrix, and has an apparent isoelectric point of pH 4.0-4.5 and 6.0-6.5. These observations indicate that in addition to the intrafollicular steroidal mileau a variety of nonsteroidal compounds, secretory products of the granulosa cells or other ovarian compartments, contribute to the regulation of folliculogenesis.

EXAMPLE FOUR

The Effect of the Follicular Inhibitory Protein Fraction as an Aromatase Inhibitor In Examples One through Three, protein(s) in ovarian venous effluent, human follicular fluid and spent media from human granulosa cell cultures inhibited rat ovarian weight gain in response to gonadotropin stimulation. Follicular fluid extracts containing this protein were found to have a molecular weight of 12,000-15,000 and an isoelectric point of pH 4.5 and 6.5. As inhibin, another protein secreted by human ganulosa cells, increases with follicular maturation and decreases with luteinization, individual human follicles from untreated as well as hMG and clomiphene trated women were assessed for FP activity, and that activity was correlated with the follicles' follicular fluid steroid and inhibin concentrations.

Follicular aspirates were obtained from women (aged twenty-four-thirty-two years) who were participating in an in vitro fertilization protocol. All patients had regular ovulatory menstrual cycles based on monthly vaginal bleeding and at least a single luteal phase serum progesterone in excess of 3 ng/ml. When serial ultrasonographic examinations (ADR Model 2140 real-time sector scanner with a 3.5 mHz rotating head transducer) demonstrated a follicular diameter in excess of 18 mm laparoscopy was performed for aspiration of all follicles greater than 16 mm in diameter. Follicular aspirates were immediately transferred to an adjacent laboratory for removal of granulosa cells by centrifugation (600 x G, 15 minutes) and storage of follicular fluid (−37° C.) until assay. Follicular fluid concentrations of estradiol, progesterone, 17-hydroxy progesterone, androstenedione and testosterone were determined by established radioimmunoassay techniques.

Individual follicular fluid samples were slowly thawed and fractionated by dropwise addition of an equal volume of saturated ammonium sulfate during persistent agitation at 4° C. After a twelve hour incubation at 4° C., the precipitate was recovered by centrifugation and resuspended (2:1, vol/vol) in 10% ammonium sulfate. An additional twelve hours of mixing was followed by centrifugation at 3,000 x g for thirty minutes. The resulting supernatant was dialyzed in 10,000 molecular weight exclusion membranes against PBS (0.025 M; pH 6.8) for sixteen hours at 4° C. and then lyophilized. The retentate (50 mg in 0.5 ml aliquots) was passed through a column (9×32 mm; bed volume, 2 ml) containing agarose-immobilized matrex gel Orange A which had been equilibrated with 20 mM Tris-HCl, pH 7.5. Unbound material was eluted with 10 ml of 20 mM Tris-HCl, pH 7.5 and bound material was eluted with 10 ml 0.5 ml M KCl in 20 mM Tris-HCl, pH 7.5. Bound eluent fractions were dialyzed overnight against PBS and lyophyllized. Protein concentrations were then determined.

Aromatase Activity

Porcine granulosa cells were collected from fresh ovaries obtained at the local slaughterhouse. After washing in serum free HAMS-HEPES tissue culture media, $5 \times 10^5$ cells in 0.2 ml of medium were pipetted into 12×75 mm polystyrene tubes. Triplicate 200 ul portions of each follicular fluid preparation at three different protein concentrations (700-10 ug/ml) were tested. Each tube then received 100 µl of FSH(10n g) in culture medium and was incubated at 37° C. in a shaking water bath for three hours. An atmosphere of 90% $N_2$, 5% $O_2$ and 5% $CO_2$ was maintained throughout the incubation. The incubation was stopped by the addition of 0.5 ml Hams-Hepes media and centrifugation at 1000 x g for five minutes. The granulosa cells were then resuspended in 0.5 ml Hams-Hepes media, whereupon 100 µl of cells were assayed for aromatase activity. Androstenedione, the referent aromatase substrate, was added in 0.1 ml medium (final concentration, $1.0 \times 10^{-7}M$). All incubations were performed in duplicate for three hours at 37° C. in a shaking water bath (120 cycles/ minute). The reaction was stopped by transferring the tubes to an iced water bath before centrifugation (five minutes at 1000 x g). The supernatants were decanted and stored at −20° C. until measurements of estrogen were performed. Control incubations (no androstenedione added) were processed in the same way. Blank estrogen values obtained for the controls were subtracted from the corresponding values for incubations in the presence of androstenedione. Aromatase activity was expressed as estrogen production (nanograms per viable granulosa cell).

Inhibin Activity

Ten percent (weight/volume) activated charcoal (norite A) was added to the individual follicular fluids, and stirred continuously overnight at 4° C., followed by centrifugation (1000 x G, twenty minutes) and sterile filtration to remove the charcoal. The charcoal-striped follicular fluid contained less than 10 pg/ml of androstenedione, progesterone, and estradiol as determined by radioimmunoassay. Inhibin activity was determined using the degree of inhibition of basal (i.e. non-LHRH stimulated) twenty-four hour FSH secretion by dispersed rat anterior pituitary cells in primary monolayer. For each cell culture, anterior pituitary glands were obtained from 20 cycling female Sprague-Dawley rats (250-300 gm body weight). During the thirty minute interval required for removal of all the pituitary glands, each gland was placed in medium (pH 7.4, 20° C.). Pituitary glands were finely minced with scissors and incubated in a mixture containing 1% viokase, 3.5% collagenase, and 3% bovine serum albumin in medium buffer at 37° C. for thirty to forty-five minutes. The dispersed cells were counted using a hemocytometer and pituicyte viability was determined by 1% trypan blue exclusion. Typically, more than 90% of the dispersed cells were viable. The cells were diluted to a concentration of $2.5 \times 10^5$ viable cells per ml growth medium. Growth medium consisted of HAMS F10 containing 10% fetal calf serum with penicillin, fugizone and streptomycin (50 u/ml and 50 mg/ml and 50 mg/ml respectively). Cells were added to tissue culture dishes in a volume of 2.0 ml growth media, and attachment of the cells to the well surface was completed by two days. After cell attachment, the original growth media was discarded and the cells were washed twice with additional HAMS balanced salt solution. Thereafter, three concentrations of charcoal-treated follicular fluid (0.02%, 0.2%, 2%) were added to the plate. A lyophilized porcine follicular fluid standard (PFFL KT-1, provided by CP Channing) was resuspended in saline and tested in each assay at 0.003%, 0.016%, 0.08%, 0.04%, and 2% concentrations. Twenty-four hours later, the spent culture media was assayed in duplicate using the NIH-RIA kit for rFSH.

Data Analysis

The mean estrogen concentration in the serum control tube for each FP assay was set at 100%, and the response in each test was expressed as a percentage of the control estrogen concentration. The coefficient of variation for each group of three replicate tubes was calculated. If the coefficient was 15%, the estrogen assay was repeated and/or one value of the three was discarded. A curve was constructed in which the percent inhibition of estrogen in each well was plotted vs the protein concentration of follicular fluid added. Unknown values were determined by plotting the experimentally determined values at three different protein concentrations (700-10 ug/ml) on a log-linear graph and extrapolating the value at 50 ug/ml. The percent inhibition of estradiol at 50 ug of unknown follicular fluid was read off the standard curve and expressed as percent aromatase inhibition for that follicle.

For the inhibin assay, the response in each test plate was expressed as a percentage of the control FSH concentration, which was set at 100%. The coefficient of variation of each group of three replicate plates was calculated. If the coeffient was 15% the assay was repeated. A standard curve was constructed in which the percent inhibition of FSH in standard wells was plotted vs the log of the standard added. Least squares linear regression was used to construct a standard curve in the linear portion of the dose response curve. Unknown follicular fluid inhibin values were determined by plotting the experimentally determined values (0.02%, 0.2%, 2%) on a log-linear graph and extrapolating the value at 1%. The percent inhibition of rFSH at 1% of unknown follicular fluid was read off the standard curve and expressed as Channing units (1 CU = 1 unit of inhibin standard = the inhibition of rFSH in rat pituicyte culture by 1 nl of charcoal treated, ethanol extracted porcine follicular fluid).

Tests for statistical significance were performed by one-way analysis of variance and Duncan's new multiple range test. Correlation between follicular fluid steroid concentration and FP activity was performed using regression analysis with tests of statistical significance performed by t test corrected for N.

Patient Outcome

Seven patients underwent follicular aspiration during an untreated spontaneously occurring ovarian cycle. At the time of laparscopy, only one antral follicle was seen in each patient which was aspirated. Nine patients received clomiphene citrate therapy (150 mg/day, cycle days 5-9), providing a total of twenty-four follicles with diameters greater than 16 mm. All except one patient had multiple follicles aspirated. Six patients who underwent hMG therapy (150 IU LH/150 IU FSH administered daily beginning on cycle day 3 until follicle aspiration), provided twenty-three follicles. Care was taken to aspirate all follicles with diameters in excess of 16 mm. There was no difference between treatment groups in follicle size which averaged $18.7 \pm 0.9$ mm ($x \pm SEM$, range 16-24 mm). At the time of aspiration, serum estradiol levels averaged 1456 pg/ml $\pm 285$ pg/ml for all patients studied (range of 310-3200 pg/ml) with no significant difference between treatment groups.

Validation

Figure 18:
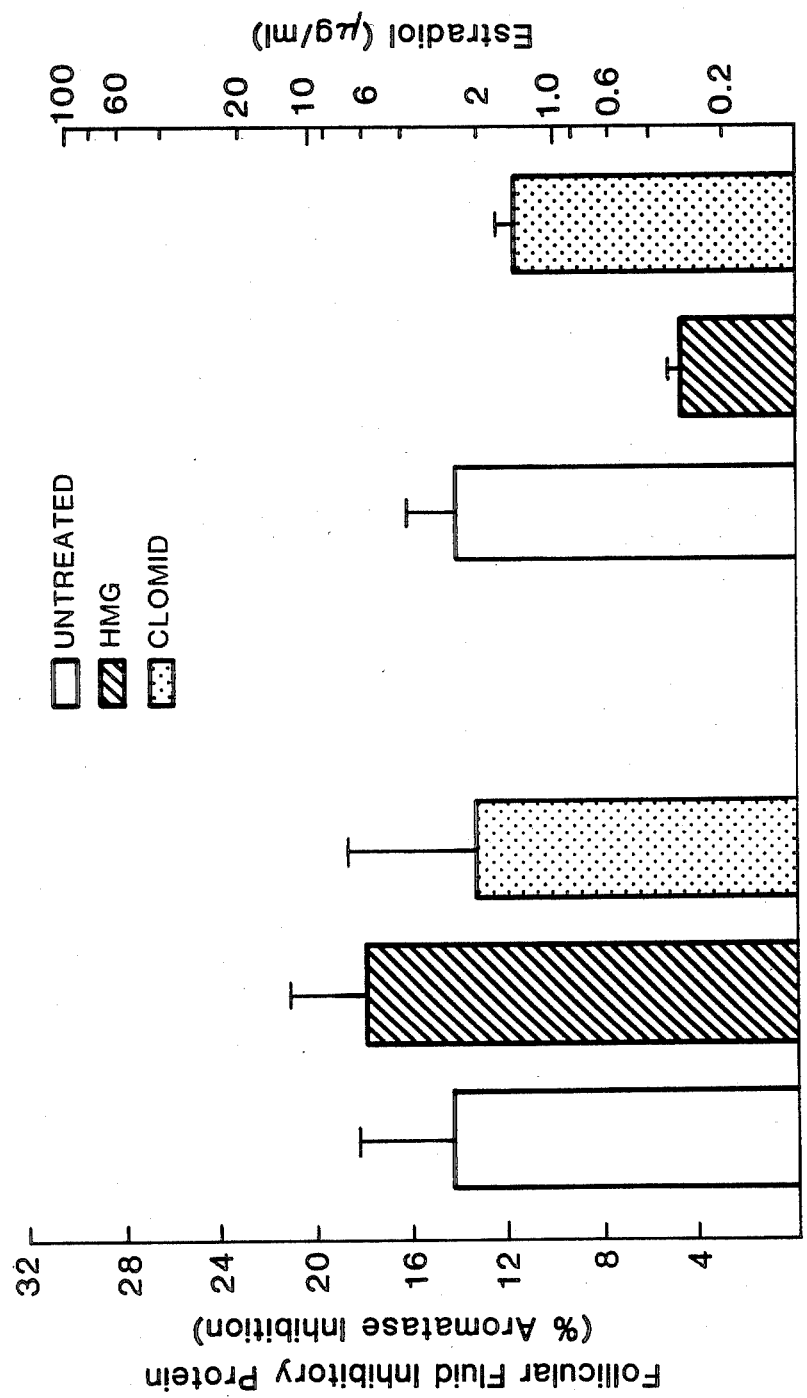
FIG. 18: Follicular fluid protein activity (% inhibition of porcine granulosa cell aromatase activity) and estradiol concentrations for untreated (open bar, n=7, 16 follicles), hMG (diagonal, n=9, 23 follicles), and clomiphene treated (dots, n=6, 7 follicles) spontaneously menstruating women. Differences between follicular fluid estradiol levels were significant (untreated vs hMG, $p<0.01$); hMG vs clomiphene, $p<0.01$; untreated vs hMG, $p<0.05$). No statistically significant differences were apparent in follicular fluid protein activities between the three groups.

To establish the number of porcine granulosa cells for the FP assay, the following porcine granulosa cell concentrations were used: $0.5 \times 10^6, 1 \times 10^6, 2 \times 10^6$ cells/ml. The total amount of estrogen produced following a three-hour incubation was $55 \pm 9$, $140 \pm 27$, $375 \pm 48$ pg/culture dish, respectively. Consequently, $2 \times 10^6$ porcine granulosa cells were used in each subsequent assay. To evaluate the effects of porcine FSH (NIH P-2 reagent) and follicular protein (100 ug), porcine granulosa cell cultures were prepared with or without porcine FSH added to the media (0.5 ml final volume), incubated at 37° C. for three hours in a shaker bath with 95% $O_2$ and 5% $CO_2$, after which androstenedione ($10^{-7}$ M) was added in 0.5 ml of growth media. Cultures were incubated for three hours at 37° C. in a shaker bath then centrifuged (1000 x G for fifteen minutes) and media collected for estrogen determination. Without FSH, the estrogen production was $439 \pm 41$ pg/ml; with follicular protein added, the estrogen production was $22.4 \pm 41.7$ pg/ml. When 2 units/ml of porcine FSH were added without follicular protein, 728 pg/ml estrogen were produced. Addition of follicular protein produced a dose-response relationship as is shown in FIG. 18: 1000 ug follicular protein: 200.26 pg/ml; 200 ug follicular protein: 306.37 pg/ml; 50 ng follicular protein: 345.41 pg/ml; 10 ug follicular protein: $334 \pm 18$ pg/ml of estrogen. Accordingly, individual patient values were extrapolated to 50 ng/ml of follicular protein for comparisons of activity.

The follicular fluid protein elution profiles from Orange A were analyzed using three different concentrations of KCl: 0.17 M KCl yielded 3.1 mg protein/ml which had a 37% inhibition of aromatase, 0.5 M KCl eluted 6 mg protein/ml which had an 84% inhibition of aromatase and 1.5M KCl eluted 0.05 mg protein/ml which had a 6.7% inhibition of aromatase. Accordingly, the 0.5 M KCl fraction was used to elute the active material from the Orange A bound column. KCl (0.5M) was found to have no effect in the granulosa cell aromatase assay: control (without KCl, 3 determinations, $710 \pm 41$ ng/ml. with KCl, $712 \pm 38$ ng/ml). Duration of incubation time was assessed with and without FSH. Two hour assay incubations yielded 2 ng estrogen/ml; twenty-four hours: 5.3 ng estrogen/ml. With 2 ng FSH added, 39 ng estrogen/ml at two hours and 6 ng FSH/ml produced 8 ng estrogen/ml at twenty-four hours. With 1 ng FSH/ml, $35 \pm 1.8$ ng estrogen/ml were produced at two hours and $4.7 \pm 0.9$ ng estrogen/ml at twenty-four hours. Accordingly, a three-hour incubation was used to determine specific FP activity.

When the follicular fluid preparation was heated to 56° C. $\times$ 1 hour, the inhibition of granulosa cell aromatase was lost.

In FIG. 18, the follicular fluid protein activity (% inhibition of porcine granulosa cell aromatase activity) and estradiol concentrations in untreated (open bar, n=7, 16 follicles), hMG (diagonal, n=9, 23 follicles), and clomiphene (dots, n=6, 7 follicles) treated women are shown. Differences between follicular fluid estradiol levels were significant (untreated vs hMG, $p < 0.01$; hMG vs clomiphene, $p < 0.01$; untreated vs hMG, $p < 0.05$). No statistically significant differences were apparent in follicular fluid protein activities betweeen the three groups.

Follicular Protein Activity

Figure 19:
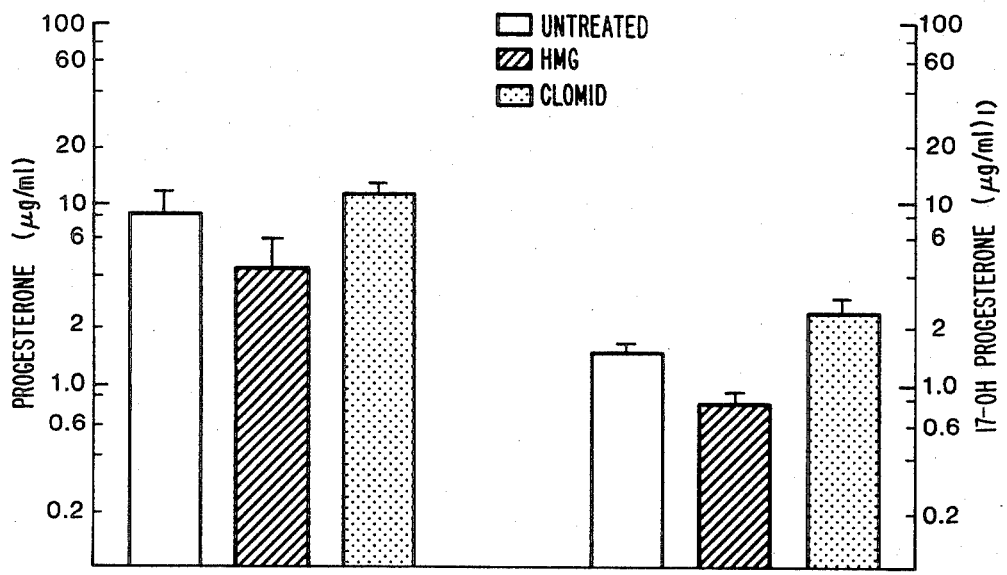
FIG. 19: Follicular fluid progesterone and 17-hydroxyprogesterone concentrations from untreated, hMG, and clomiphene treated spontaneously menstruating women. Differences in progesterone values were significant for the hMG vs clomiphene ($p<0.05$) and hMG vs untreated ($p<0.05$) patients. All the follicular fluid 17-hydroxyprogesterone values were significantly different (untreated vs clomiphene, $p<025$; hMG vs clomiphen, $p<0.01$; hMG vs untreated, $p<0.025$).
Figure 20:
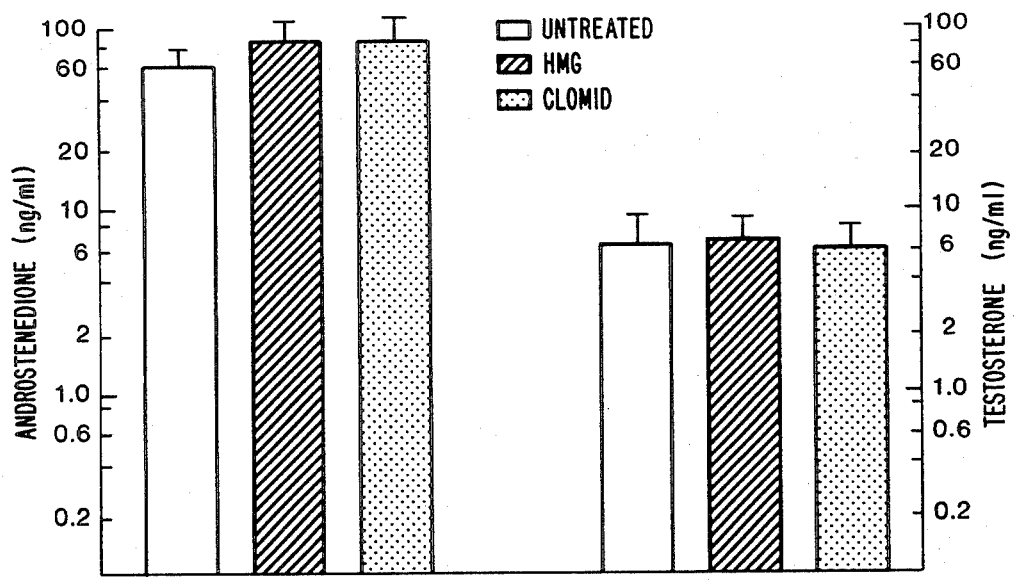
FIG. 20: Follicular fluid androstenedione and testosterone concentrations for untreated, hMG and clomiphene treated regularly menstruating women. There were not statistically significant differences between the treatment groups.
Figure 21:
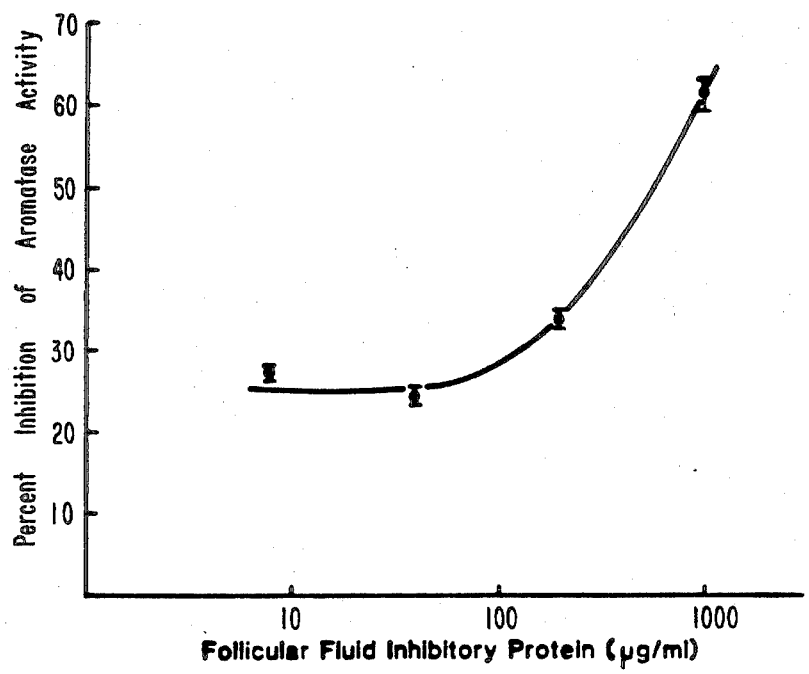
FIG. 21: Dose-response inhibition of porcine granulosa cell aromatase activity by a follicular fluid protein(s). Aromatase activity was determined in triplicate determinations with granulosa cells ($10^6$/culture), androstenediene ($10^{-7}$M) and pFSH (2 ng) co-cultured for three hours.

FIG. 19 shows the follicular fluid progesterone and 17-hydroxyprogesterone concentrations from untreated, hMG, and clomiphene treated spontaneously menstruating women. Differences in progesterone values were significant for the hMG vs clomiphene ($p < 0.05$) and hMG vs untreated ($p < 0.05$) patients. All the follicular fluid 17-hydroxyprogesterone values were significantly different (untreated vs clomiphene, $p < 0.025$); hMG vs clomiphene, $p < 0.01$; hMG vs untreated, $p < 0.025$). The follicular protein activity levels (% inhibition of porcine granulosa cell aromatase by 50 ug of follicular fluid) for untreated patients was $14.16 \pm 5.32\%$ ($X \pm SEM$). For patients receiving hMG, follicular protein activity levels were $18.09 \pm 3.46\%$, and for patients receiving clomiphene, $13.7 \pm 5.36\%$. There was no statistically significant difference in the values between the three treatment groups. The amount of estradiol in the follicular fluid of untreated patients was $2.59 \pm 1.2$ ug/ml, for patients receiving hMG therapy, $0.34 \pm 0.5$ ug/ml, for patients receiving clomiphene, $1.31 \pm 0.34$ ng/ml. These values were all significantly different ($p < 0.05$, untreated vs clomiphene, clomiphene vs hMG; $p < 0.01$ untreated vs hMG). Progesterone values for untreated patients were $9.84 \pm 3.35$ ug/ml, for hMG-treated patients, $5.18 \pm 1.1$ ug/ml, and for clomiphene-treated patients, $11.3 \pm 2.3$ ug/ml (FIG. 19). These differences were significant for the unstimulated and hMG treated patients ($p < 0.05$) and hMG vs clomiphene treated patients ($p < 0.01$). The 17-hydroxyprogesterone concentrations FIG. 20) for patients receiving no additional therapy were $1.66 \pm 25$ ug/ml, for those receiving clomiphene therapy $2.6 \pm 3$ ug/ml, and for those receiving hMG therapy: $0.76 \pm 0.11$ ug/ml. All these values were significantly different (hMG vs clomiphene $p < 0.01$; hMG vs unstimulated $p < 0.01$; unstimulated vs clomiphene $p < 0.025$). Follicular fluid androstenedione concentrations in untreated patients were $61.9 \pm 43$ ug/ml (FIG. 21). For hMG and clomiphene treated patients they were $85.5 \pm 37$, and $84.8 \pm 43$ ng/ml, respectively. Follicular fluid testosterone levels from untreated patients were 7.34 ng/ml$\pm 3.7$ (FIG. 21). For the treated patients, there was no difference in the follicular fluid testosterone concentrations in patients receiving either hMG ($7.09 \pm 2.14$ ng/ml) or clomiphene ($6.14 \pm 1.8$ ng/ml).

Correlation of FP vs Follicular Fluid Steroids

Figure 22:
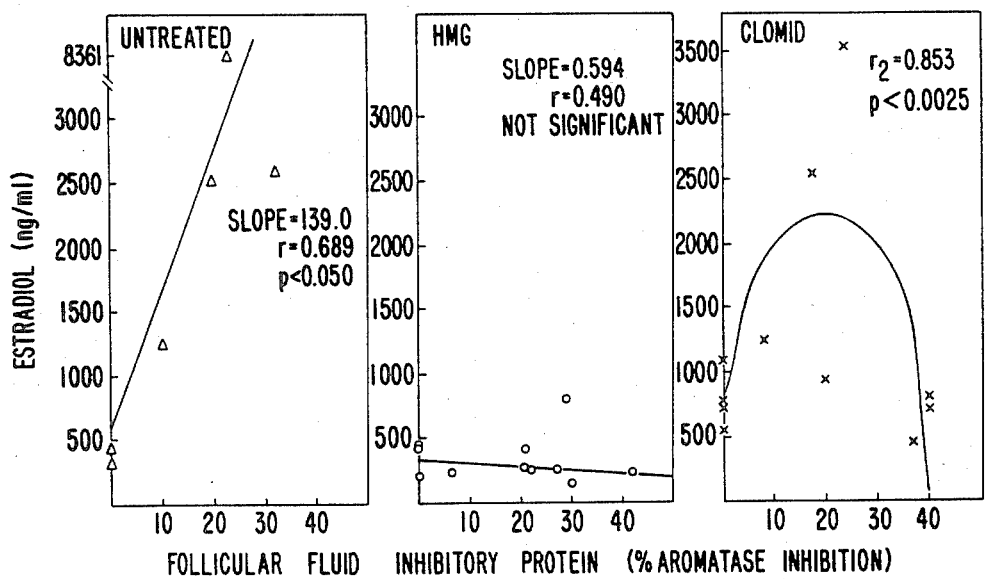
FIG. 22: Correlation between intrafollicular estradiol concentrations and the activity of a follicular fluid protein (% aromatase inhibition) from regularly menstruating patients, untreated (panel A), hMG treated (panel B) or clomiphene treated (panel C). There was a statistically significant positive correlation between follicular fluid estradiol levels and follicular protein activity ($r=0.689$, $p.<0.05$). Clomiphene treated patients had a biphasic response ($r_2=0.853$, $p.<0.0025$).
Figure 23:
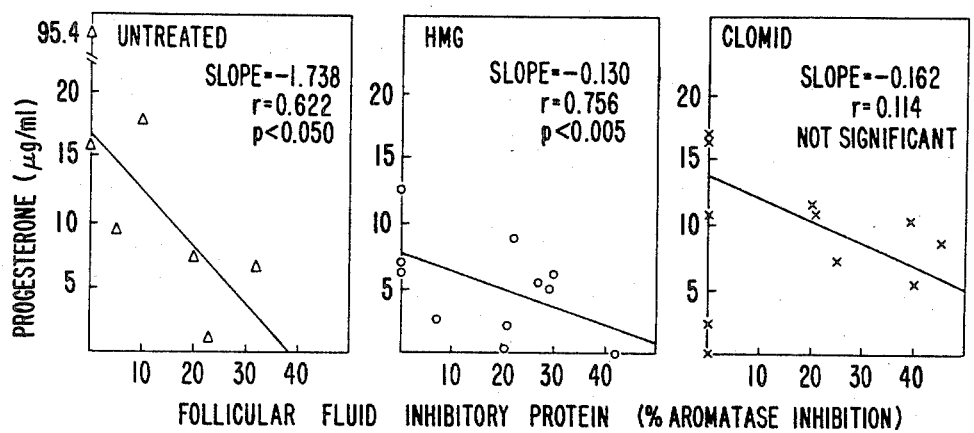
FIG. 23: Correlation between follicular fluid progesterone levels and a follicular fluid protein activity (% aromatase inhibitior) in regularly menstruating women either untreated, or after clomiphene or hMG therapy. There was a significant negative correlation between intrafollicular progesterone and follicular protein activity on untreated ($r=0.622$, $p<0.05$) and hMG treated ($r=0.756$, $p<0.005$) patients.
Figure 24:
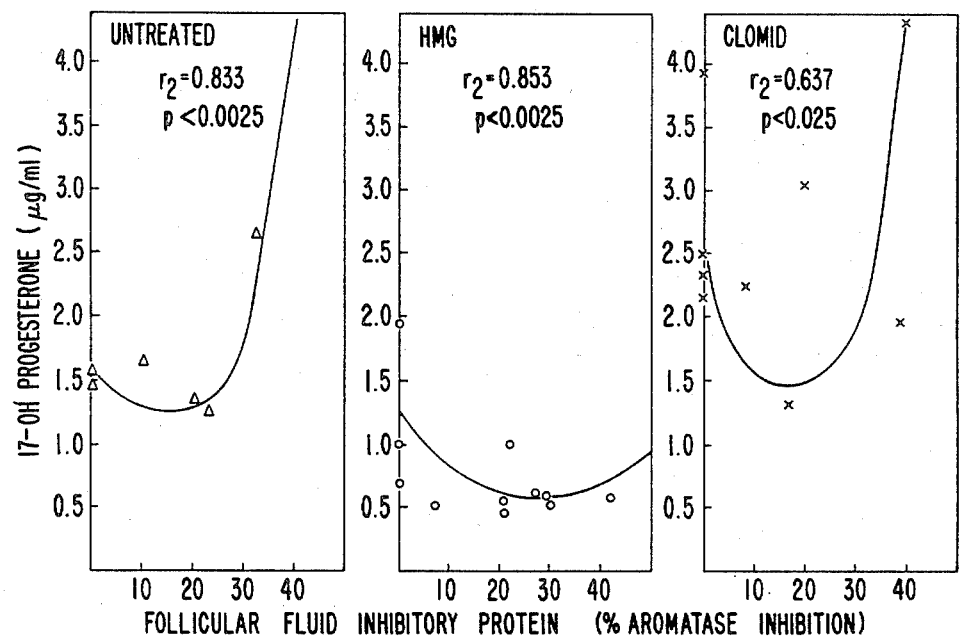
FIG. 24: Correlation between follicular fluid 17-hydroxyprogesterone concentrations and a follicular fluid protein (% aromatase inhibition) from regularly menstruating women either untreated or after receiving hMG or clomiphene therapy. All groups had a significant biphasic response as determined by second order regression analysis.
Figure 25:
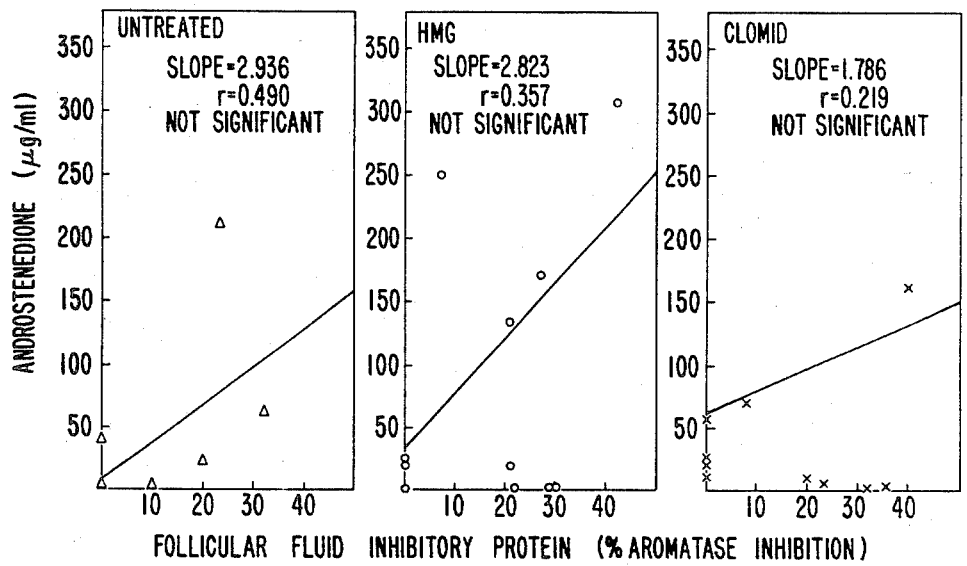
FIG. 25: Correlation between follicular fluid androstenedione concentration and a follicular fluid protein(s) (% aromatase inhibition) in regularly menstruating women untreated or after hMG or clomiphene therapy. No significant correlations were apparent.
Figure 26:
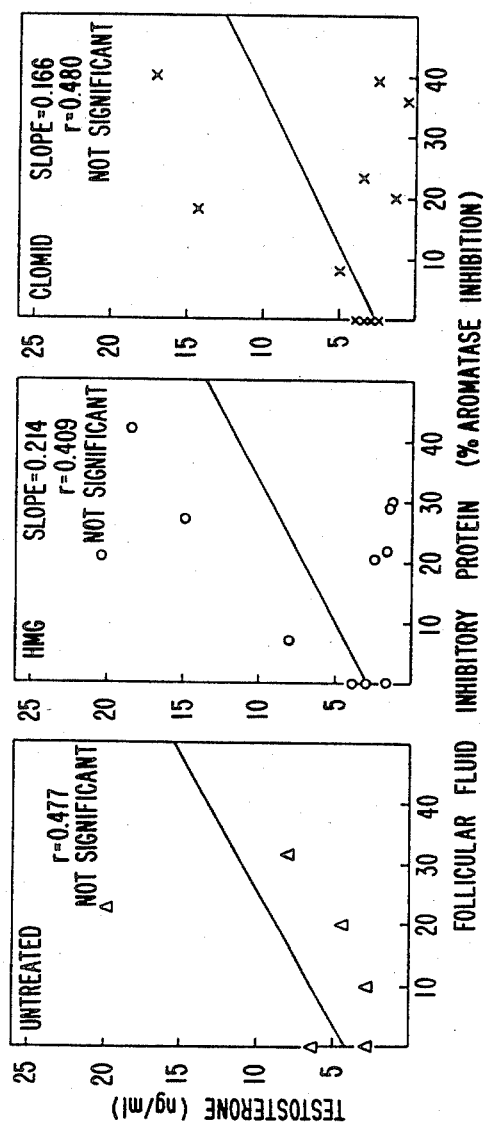
FIG. 26: Correlation between follicular fluid testosterone concentrations and a follicular fluid protein(s) (% aromatase inhibition) in regularly menstruating women untreated or after hMG or clomiphene therapy. No significant correlations were apparent.
Figure 27:
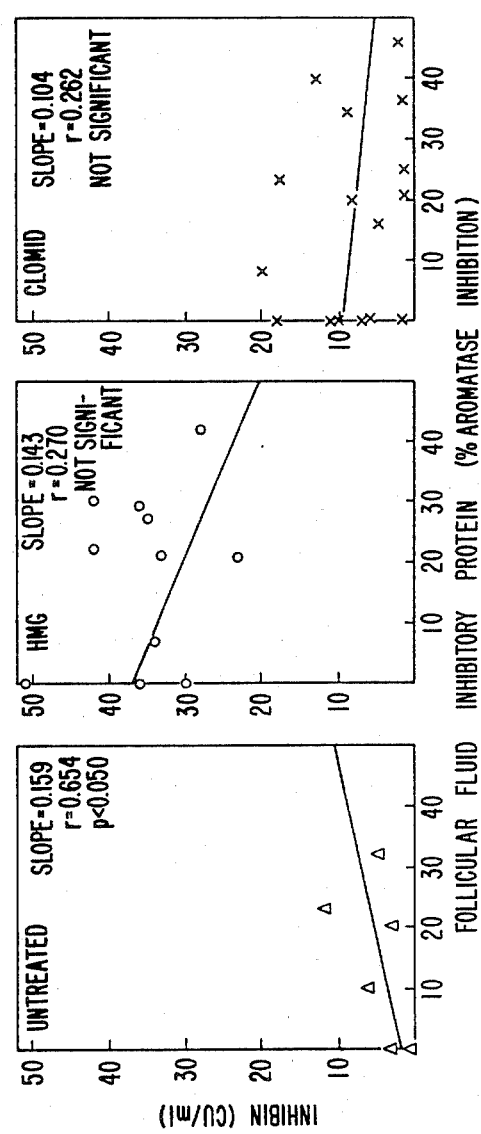
FIG. 27: Correlation of follicular fluid inhibin activity (inhibition of spontaneous rFSH release by pituicytes) and a follicular fluid protein(s) (% aromatase inhibition) in regularly menstruating women either untreated or after receiving HMG or clomiphene therapy. A statistically significant correlation was apparent between inhibin and follicular protein activities in follicular fluid from untreated patients ($r=0.650$, $p<0.05$).

There was a positive correlation between follicular fluid estradiol concentrations and follicular protein activity in untreated patients (r=0.689, p<0.01; FIG. 22). For patients receiving hMG therapy, there was no significant correlation between follicular protein levels and follicular fluid estradiol concentrations (r=490, p<0.1). For patients receiving clomiphene therapy, the correlation between follicular protein activity and follicular fluid estradiol was described by two populations using a second degree regression analysis ($r_2 \leq 0.853$, p<0.01). Correlation between follicular fluid progesterone concentrations and follicular protein activity for untreated patients (r=0.622, p<0.05) and hMG treated patients (r=0.756, p<0.005) was significant (FIG. 23). For clomiphene treated patients, corelation between follicular fluid progesterone and follicular protein activity were not significant. The correlation between follicular fluid 17-hydroxyprogesterone values and follicular protein activity for the untreated (r=0.833, P<0.001), as well as hMR ($r_2$=0.853, p<0.0025) and clomiphene ($r_2$=0.637, p<0.25) treated patients was significant (FIG. 24) by second order regression analysis. The correlation between follicular fluid follicular protein activity and androstenedione concentration from untreated (r=0.241), hMG (r=0.357), and clomiphene (r=0.219) treated patients was not significant (FIG. 25), nor was the correlation between testosterone and follicular protein activity significant (r=0.477, 0.409, 0.480, respectively; FIG. 26). The average inhibin activity for untreated patients was 50±1.9 CU. In patients receiving treatment, inhibin activity was 8.2≈2.3 and 35.4±3.7 CU for clomiphene and hMG treatment, respectively. Difference between hMG and either clomiphene or untreated patients were highly significant (p<0.001). Correlation between inhibin and follicular protein activities for untreated patients was significant (r=0.654; p<0.05; FIG. 27). However, there was no statistically significant correlation between inhibin and follicular protein activities in patients receiving either hMG (r=0.270) or clomiphene (r=0.262).

These observations report the presence of an aromatase inhibitor in a purified fraction of human follicular fluid. This follicular fluid protein fraction has previously been shown to inhibit hMG-mediated increases in rat ovarian weight and serum estradiol concentrations. As is shown hereinafter in Example eight, when this protein fraction is injected into regularly menstruating monkeys, it disrupts folliculogenesis resulting in either anovulatory cycles or luteal phase insufficiencies accompanied by low serum estradiol and progesterone concentrations without markedly altered peripheral serum gonadotropin levels. This data, taken together with those presented previously (Examples One-Three), suggest that the developing granulosa cell, through production of an aromatase inhibitor, is capable of autoregulating the estrogen production of its own and other follicles.

Example Five

Regulatory Protein Fractions in Porcine Follicular Fluid

Example Two details the isolation of a protein fraction from human follicular fluid, which suppresses follicular response to gonadotropins. The present example employs an identical isolation, bioassay and HPLC procedures with respect to porcine follicular fluid (PFF). Isoelectric focusing demonstrated inhibitory activity at pH 3.7–4.0 and peak activity was found in the molecular weight range 12,000–18,000.

Granulosa cells were isolated from rat ovaries and FSH binding was determined by the procedure of Erickson, as descirbed in Example Three. Aromatase activity of the rat granulosa cells was determined in a procedure identical to that described in Example Three.

Table 3 sumarizes the results of dye-ligand matrix chromatography of the 10–55% saturated ammonium sulfate porcine follicular fluid fraction. Although Orange A bound only 13% of the charged protein, 1.5 M KCl elution recovered bioactive material which contained the greatest inhibition of hMG-induced rat ovarian weight response (p<0.05) when compared to the other dye-ligand eluents. When these same fractions were treated with heat (56° C.) or trypsin (10 mg%), no suppression in ovarian weight was found.

Figure 28:
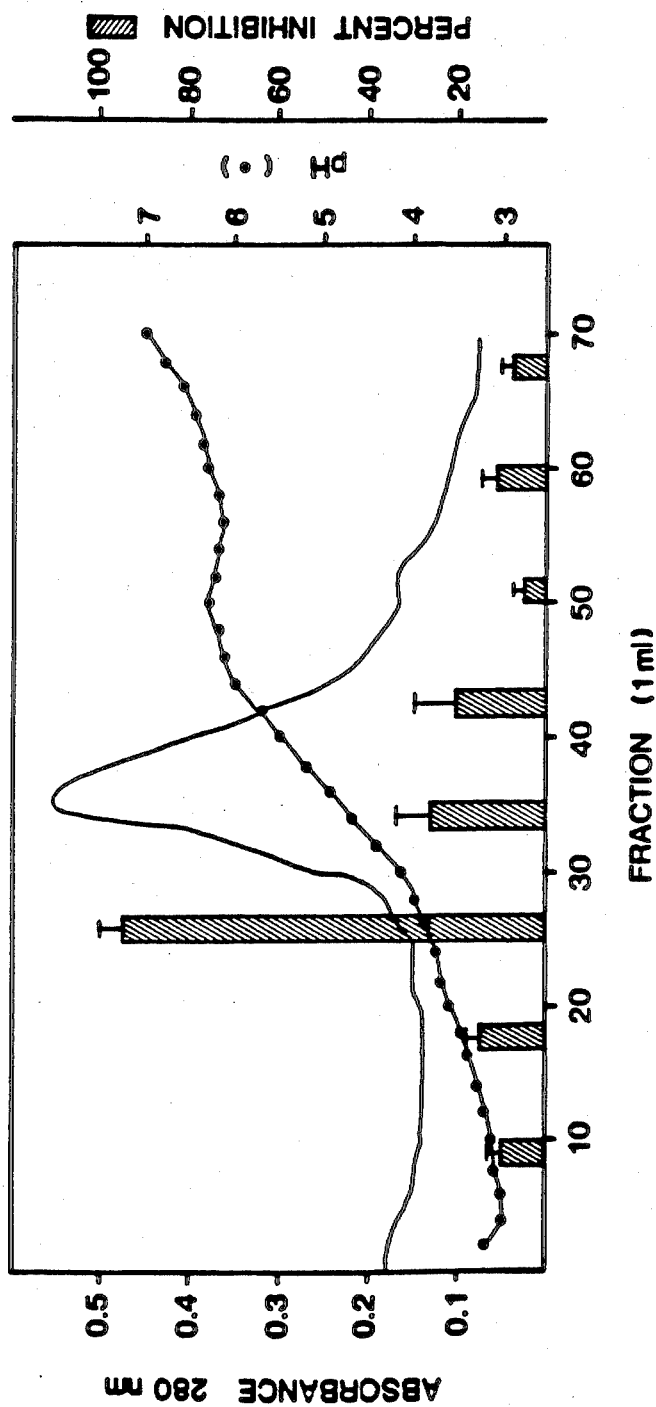
FIG. 28: Isoelectric focusing chromatogram of dialyzed ($>10,000$)mw 10–55% saturated ammonium sulfate fraction of pooled porcine follicular fluid (5 ml) after elution (1.5 M KCl) from an Orange A dye matrix column. Maximum ovarian weight inhibition (hatched bars) in immature, hypophysectomized, DES-treated rats by eluent fractions were found in the 3.7–4.0 pH range ($\overline{X}\pm$SEM of rats/fraction).

FIG. 28 depicts the chromatographic elution profile of PFF at 280 nm developed through Sephadex G-100 following the 10–55% SAS cut, dialysis, and elution of Orange A-bound material with 1.5 M KCl. An initial peak can be seen at a $V_e/V_o$ of 1.1 to 1.17, thereafter trailing, followed by a gradual ascending second plateau at $V_e/V_o$ 1.7 to 1.9. When biological activity was assessed in the HIFR-hMG bioassay, 95% inhibition of both ovarian weight and trunk serum estradiol-17-B levels were found at $V_e/V_o$ of 1.5. The same column was then equilibrated with molecular weight standards and developed with 0.025 M PBS, pH 7.4, allowing for estimation of the $K_{av}$ ($V_o - V_e/V_e - V_o$) of fractions containing inhibitory activity. The molecular weight of inhibitory activity was estimated to be between 20,000 and 40,000 daltons.

Figure 29:
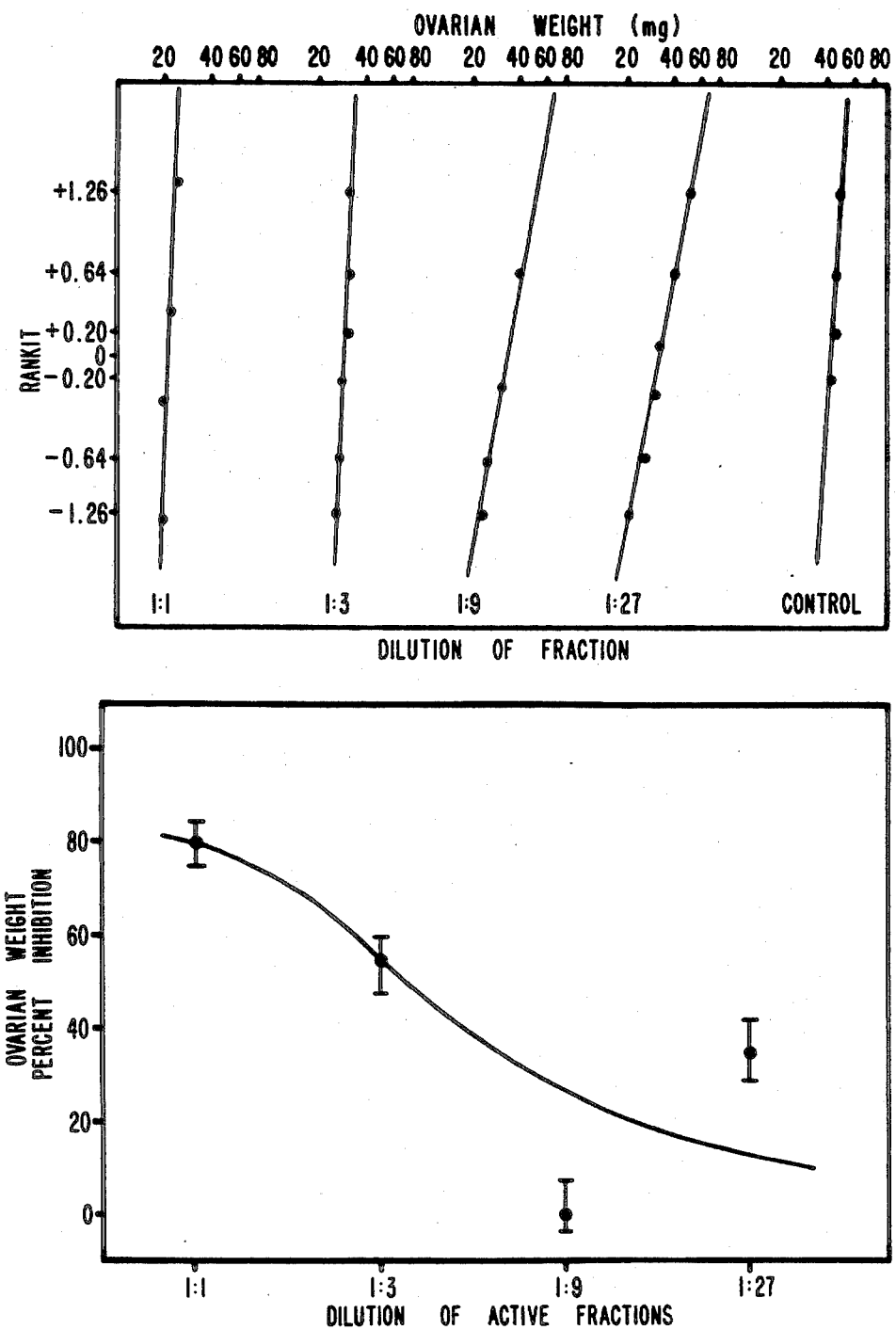
FIG. 29: Dose response relationship:porcine follicular fluid fractions which contained inhibitory activity in the rat ovarian weight augmentation bioassay recovered from isoelectric focusing (ph 3.7–4.0) after Orange A Dye Matrix elution (1.5 M KCl) and dialysis ($>10,000$ mw) of 10–55% saturated ammonium sulfate. Insert is rankit analysis of ovarian weights from dilutions tested, the O intercept of which was plotted on the dose response curve.
Figure 30:
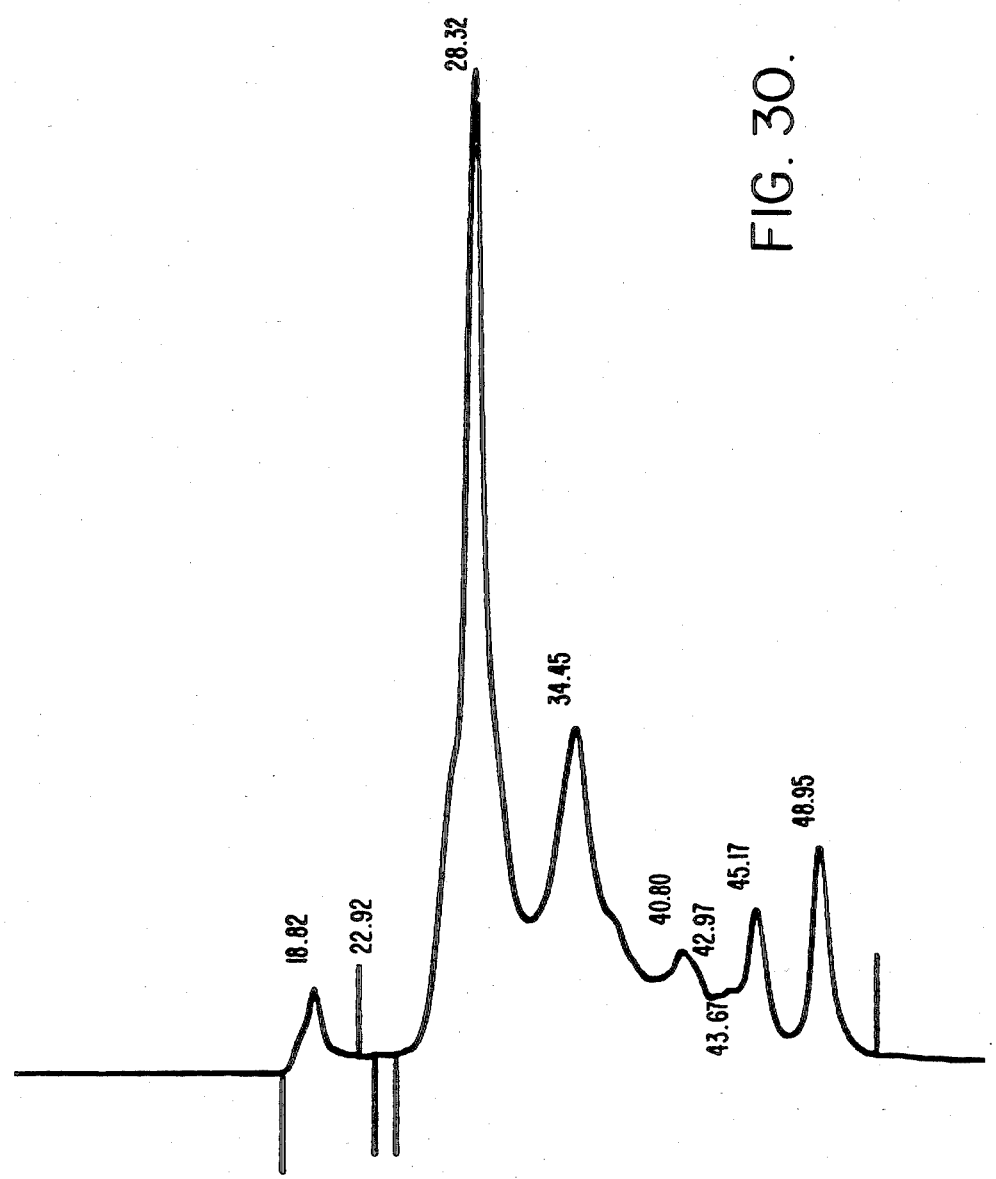
FIG. 30: High performance liquid chromatogram (gel permeation) of the Orange A-bound fraction of 10–55% saturated ammonium sulfate of porcine follicular fluid recovered from Sephadex G100 elution (Ve/Vo 1.3–1.7) Retention times corresponded to the following molecular weight ranges: 25–27. 8 min: 100,000–74,000; 27. 8–31 min: 74,000–36,000; 31–36 min: 36,000–18,000; 36–39 min: 18,000–12,000; 39–43 min: 12,000–5,800.

When eluents from the isoelectric focusing (IEF) of the Orange A bound PFF extraction (FIG. 29) were evaluated for bioactivity by rat bioassay, only fractions within the range of pH 3.7 to 4.0 contained obvious inhibition of both rat ovarian weight response and trunk serum estradiol-17B levels (83.6±9.4% and 47.2% respectively). Serial dilutions of the extracted PFF fractions eluted from the Orange A dye-matrix with 1.5 M KCl recovered from the isoelectric focusing column were tested for activity in the hypophysectomized immature DES-treated female (HIFR-rat) bioassay. A dose response relationship was apparent (FIG. 30) with fractions in the pH 3.5–4.0 range, while other pH ranges from the IEF column were without inhibitory activity.

When aliquots from the ammonium sulfate 10–55% cut eluted from the Orange A dye matrix were passed through Concanavalin-linked Sepharose 4B (eluted 3×Vo with PBS followed by 0.2 M alpha-methyl mannoside), no inhibitory activity in the rat bioassay was noted in the Con A bound fraction (i.e. eluted with mannoside) with only marginal recovery of activity (20–30% inhibition of ovarian weight response) in the material eluted in the unbound PBS fraction (data not shown).

Figure 31:
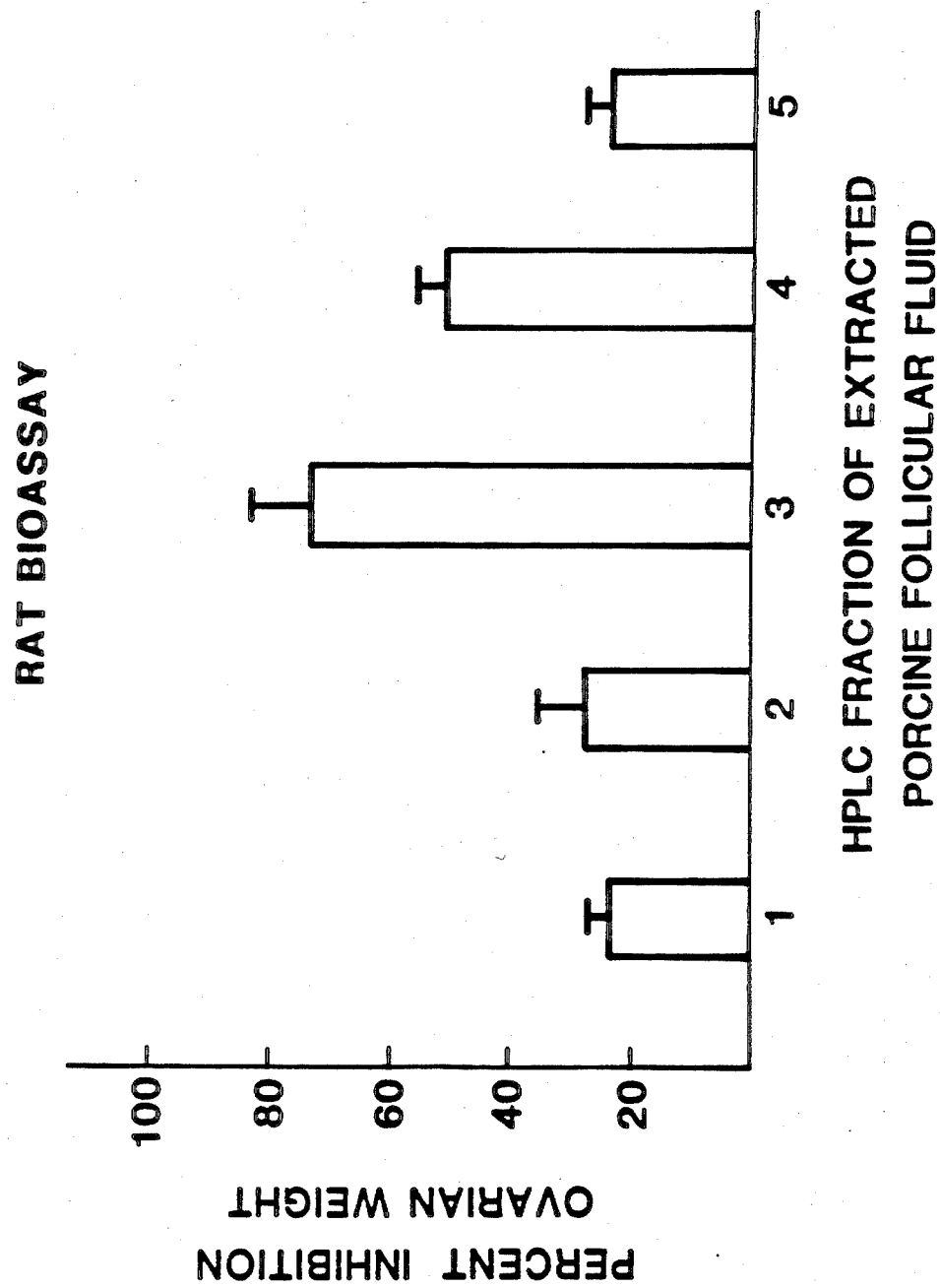
FIG. 31: Bioassay results of high performance liquid chromatography fraction of Orange A-bound porcine follicular fluid after separation by Sephadex G-100 chromatography (Ve/Vo 1.3–1.7). Inhibition of LH/FSH induced ovarian weight augmentation (X±SEM) in immature, hypophysectomized, DES-treated rats (n=6/fraction tested) was measured after treatment with 2 ml of HPLC eluents which corresponded to the following molecular weights: 1: 100,000–74,000; 2: 74,000–36,000; 3: 36,000–18,000; 4: 18,000–12,000; 5: 12,000–5,800.

FIG. 31 depicts the HPLC elution profile of the Orange A-bound extracted PFF material after separation through the Sephadex G-100 column ($V_e/V_o$ 1.3–1.7). The HPLC eluent was divided into five fractions based on peak absorbances (1: retention time - 25.0–27.8 minutes; 2: 27.8–31.0 minutes; 3: 31.0–36.0 minutes; 4: 36.0–39.0 minutes; 5: 39.0–43.0 minutes). These fractions corresponded to the following molecular weight ranges: 1: 100,000–74,000; 2: 74,000–36,000;

3: 36,000–18,000; 4: 18,000–12,000; 5: 12,000–5,800. The retention times of peak absorbances after HPLC elution, when correlated to molecular weight standards, were highly reproducible (five runs).

Figure 32:
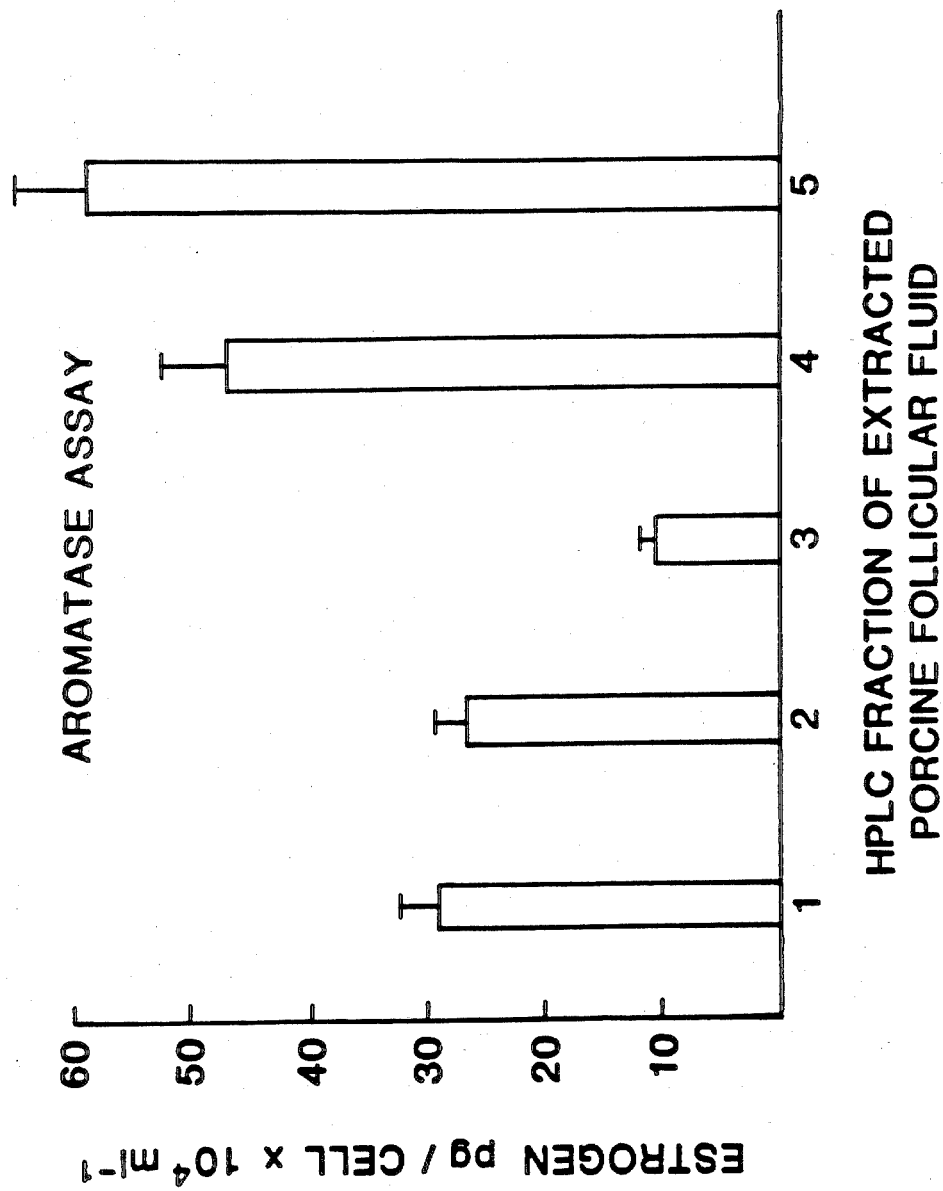
FIG. 32: Aromatase activity of rat granulosa cells derived from immature, hypophysectomized, DES-treated rats (n=6/fraction tested) which received LH/FSH stimulation and injection of high performance liquid chromatography fractions (2 ml) of extracted porcine follicular fluid (X±SEM). HPLC fractions corresponded to the following molecular weights: 1: 100,000–74,000; 2: 74,000–36,000; 3: 36.000–18,000; 4: 18,000–12,000; 5: 12,000–5,800.
Figure 33:
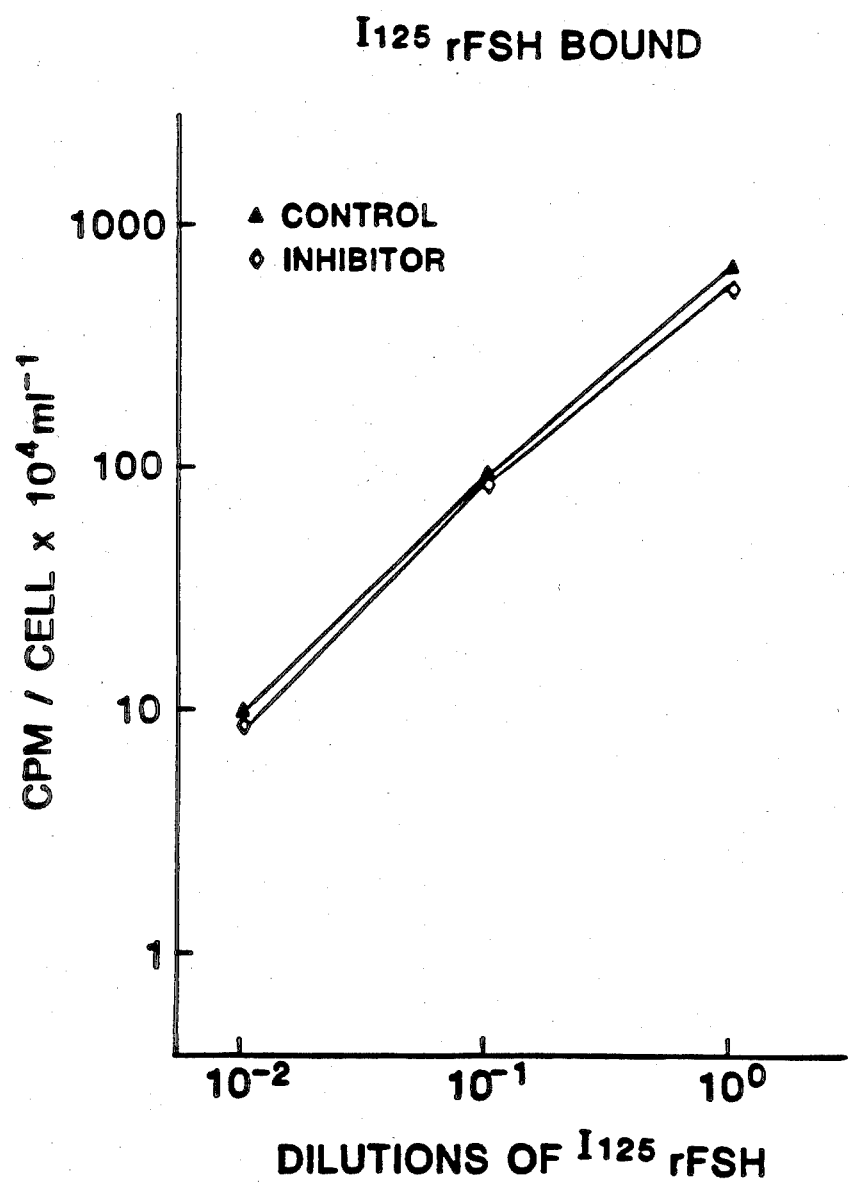
FIG. 33: Binding of FSH to granulosa cells collected from the immature, hypophysectomized, DES-treated rats (n=6) which received LH/FSH (2 Iu) and extracted porcine follicular fluid after Sephadex G-100 separation (Ve/Vo 1.3–1.7) (2 ml). Specific binding of rFSH to granulosa cells was determined by incubating 3 concentrations of labeled rFSH in the presence and absence of excess unlabeled rFSH.

When HPLC fractions were tested in the bioassay (see FIG. 32), inhibition of ovarian weight gain was evident in rats injected with fraction 3 ($74\pm8\%$; $p<0.01$) and fraction 4 ($51\pm9\%$, $p<0.05$) as compared to the other three fractions. Inhibition of androstenedione conversion to total immunoreactive estrogen (FIG. 33) by granulosa cells harvested from the HPLC-fraction treated rat's ovaries (n=6 ovaries/HPLC fraction) was evident in HPLC fraction 3 ($11.1\pm3$ pg/10,000 cells/ml). When no test fractions were injected into the HIFR-hMG bioassay rat prior to the aromatase assay, a range of 30–60 pg of total immunoreactive estrogen/10,000 cells/ml was present in the control incubates.

Figure 34:
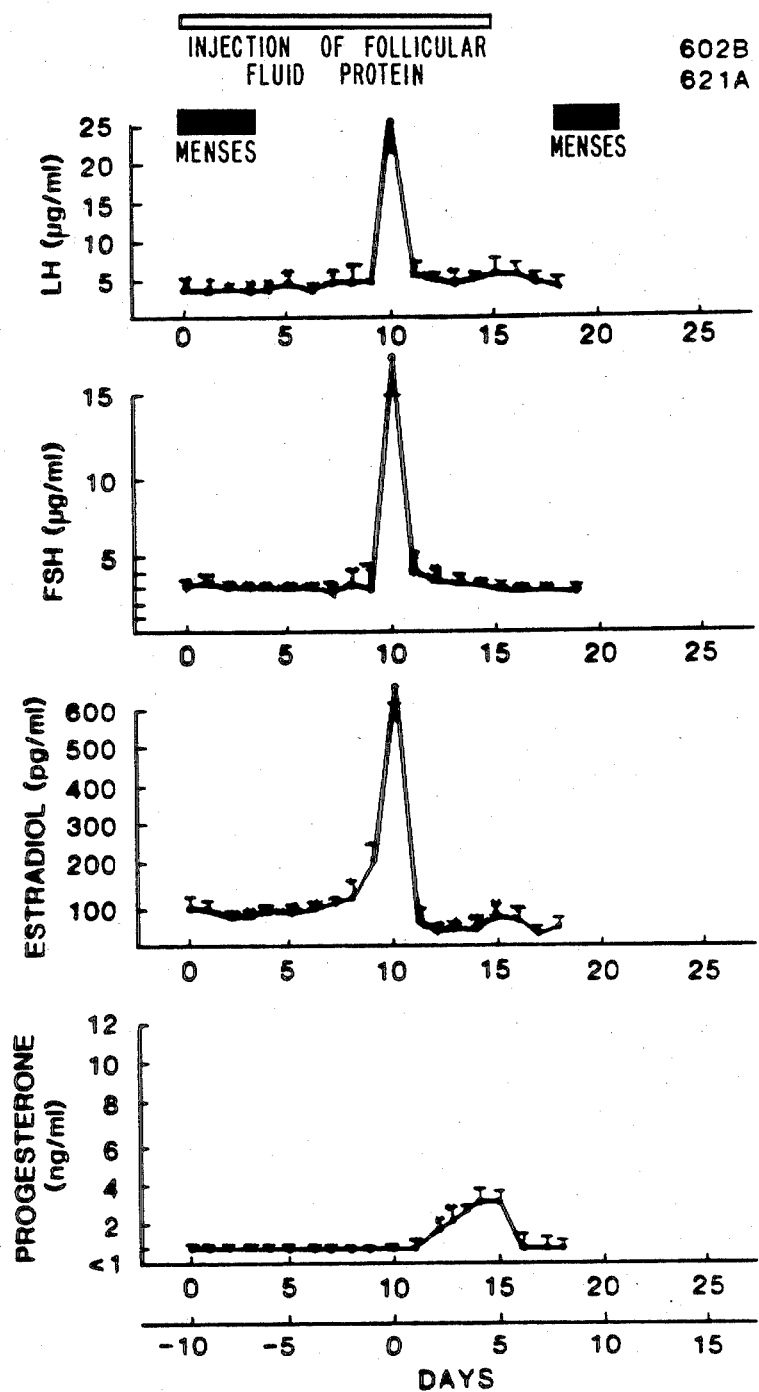
FIG. 34: Composite (X±SEM) of serum LH, FSH, estradiol, and progesterone levels from 2 rhesus monkeys which received twice daily injections (3 mg, intramuscularly) (cycle days 1–4) of a protein(s) partially purified from porcine follicular fluid which does not contain inhibin F activity. Bar indicates menses. Shaded area in each panel is the 95% confidence intervals for the respective hormone levels determined for untreated, normally cycling monkeys. Data have been synchronized to the LH surge (day 0).

FIG. 34 shows the results of FSH binding studies performed on the granulosa cells removed from the HIFR-hMG rats used in the bioassay of the Sephadex-(G100 fraction which contained inhibitory activity. No difference in FSH binding to the rat granulosa cells was evident between the control and inhibitor treated HIFR-hMG rats.

EXAMPLE SIX

Stimulation of Beta-ol-Dehydrogenase ($3\beta$ol) Activity By Follicular Protein Porcine granulosa cells were cultured with and without hCG(1000 mIU) and/or follicular protein (see Example Five for preparation from porcine follicular fluid) (2 mg) for twenty-four hours. Thereafter pregnenolone ($10^{-5}$M) was added for an additional four hours or twenty-four hours. The spent culture media was then assayed for progesterone by radioimmunoassay. At four hours there was no difference in progersterone concentration in the control and hCG treated cultures ($0.2\pm0.01$ ug, $X\pm SEM$). The progesterone levels in hCG+follicular protein and follicular protein only treated cultures ($6\pm1$ug and $46\pm$ug/culture) were markedly elevated compared to the controls ($P<0.01$). No hCG effect on $3\beta$-OL activity was evident at four or twenty-four hours of culture with pregnenolone, however at twenty-four hours follicular protein markedly stimulated granulosa cell $3\beta$-ol dehydrogenase. Thus, in addition to inhibiting the activity of aromatase in both human and porcine granulosa cells and therefore the ovarian production of estrogen, follicular protein also stimulates the activity of granulosa cell $3\beta$-ol dehydrogenase and therefore disrupts the normal process of follicle maturation.

EXAMPLE SEVEN

Granulosa Cell Inhibition of LH/hCG Receptors by Follicular Protein

Pooled porcine follicular fluid (PFF), was fractionated by drop-wise addition of an equal volume of saturated ammonium sulfate (SAS) during persistent agitation at 4° C. Following a twelve hour incubation at 4° C, the precipitate was pelleted, the supernatant discarded, and the pellet resuspended (2:1, vol:vol) with 0.025 M Tris/HCl, pH 7.5 (Buffer A). An additional twelve hours of agitation was followed by centrifugation at 3000 x G for thirty minutes. The resulting supernatant was dialyzed (Visking dialysis tubing, 10,000 molecular weight exclusion) against three changes of Buffer A for sixteen hours. Insoluble material was removed from the retentate by centrifugation (3,000 x G, thirty minutes).

Orange A columns were equilibrated with 20 mM Tris/HCl pH 7.5 then charged with 1.0 ml aliquots of the dialyzed retentate. Unbound material was eluted with 10 ml of Buffer A. The bound protein was eluted with 1.5 M KCl added to Buffer A. Eluent fractions were dialyzed overnight against Buffer A, then lyophylized.

Granulosa Cell Cultures

The granulosa cells were counted using a hemocytometer and viability was determined by 1% trypan blue exclusion. Cells were cultured ($2\times10^5$) in 2 ml of Medium 199 containing 10% fetal calf serum with penicillin and streptomycin (100 g/ml and 100 U/ml respectively) in 12×75 mm Falcon tissue culture dishes. FSH (10 ng), follicular proteins (1 mg) and or estradiol ($10^{-7}$M) was added where indicated at the initiation of culture. Media was changed after seventy-two hours.

Binding Analyses

Porcine granulosa cells were suspended in appropriate volumes of PBS-0.1% gelatin (PBS-gel). All assays were run with five concentrations of labeled hCG (10 ul), buffer (PBS-0.1% gel, 100 ul), and cells. Reactions were initiated by the addition of granulosa cells and were carried out for four hours at 25° C. All reaction tubes were precoated with 5% BSA to reduce non-specific absorption. Reactions were terminated by adding one ml of cold PBS followed by centrifugation at 30,000 x g for ten minutes. The supernatant was carefully aspirated and the pellet rewashed with one ml of PBS. The final pellet was counted in a gamma counter. Specific binding was calculated as the difference between binding in the presence (non-specific) and absence (total) of an excess of unlabeled hormone. Data were analyzed by Scatchard plots. Duplicate determinations were performed in three separate assays at each time interval.

Figure 37:
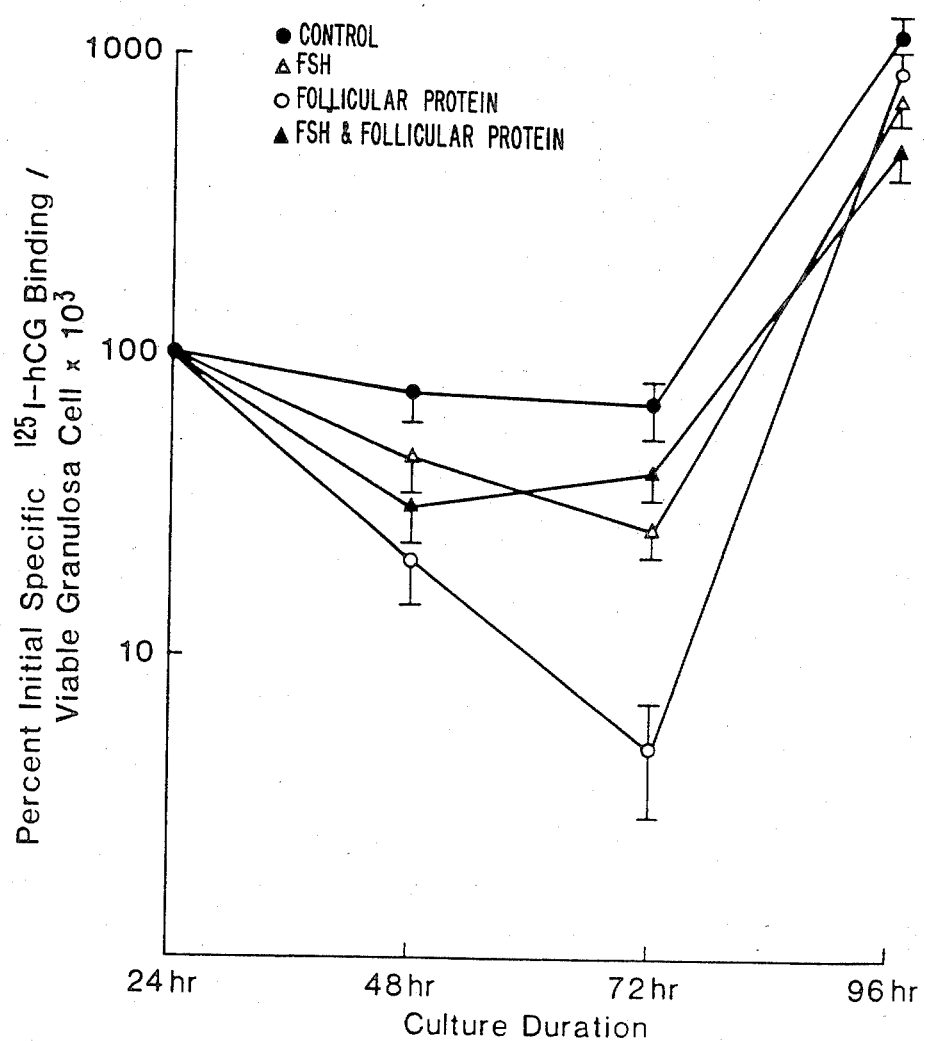
FIG. 37. Relative change in porcine granulosa cell hCG binding during 96 hr of culture with FSH, follicular protein or both. The transient decline in hCG binding is significantly reduced at 72 hr of culture in the presence of the follicular protein (P <0.05).

Follicular protein significantly reduced porcine granulosa cell hCG binding by seventy-two hours of culture. This effect was prevented with the co-administration of FSH (FIG. 37).

By ninety-six hours of culture, no change in porcine granulosa cell hCG binding was apparent with FSH, follicular protein, or both compared to control cultures demonstrating cellular recovery after removal of follicular protein at seventy-two hours of culture.

Thus, in addition to regulating key enzymatic steps in the steriodogenic pathway (aromatase, $3\beta$-ol dehydrogenase), general granulosa cell response to trophic LH stimulation is also mediated by follicular protein through inhibition of LH receptor function.

EXAMPLE EIGHT

Inhibition of the Primate Ovarian Cycle by a Porcine Follicular Fluid Protein Fraction The Examples heretofore presented report the identification of a heat and trypsin labile protein extracted from porcine (Example Five) and human (Examples Two and Three) follicular fluid which inhibited ovarian response to gonadotropins. The activity of this protein, secreted by human granulosa cells, increased with increasing follicular fluid estradiol levels and decreased with increasing follicular fluid progesterone levels (as shown in Example Four) both in vivo and during granulosa cells' luteinization in vitro (Example Three). This material has also been found to inhibit granulosa cell aromatase activity in both porcine (Examples Four and Five) and human (Example Three) granulosa cells in vitro. Follicular fluid extracts containing this activity are shown in said Examples to have a molecular weight of 12,000–15,000 and an isoelectric point of pH 4.5 and 6.5 suggesting the biophysical nature of this protein is not inhibin. In the present Example, the effects of this follicular protein fraction on the integrated hypothalamic-pituitary-ovarian axis of the normally cycling monkey are assessed.

Adult female rhesus monkeys (Macaca mulatta; n=8) were selected because of reproductive characteristics indicating normal ovarian function and menstrual regularity. The procedure for the extraction of the inhibitory follicular fluid protein fraction from porcine follicular fluid has been described in Example Five.

Five monkeys were treated with the extracted porcine follicular fluid protein fraction and three monkeys served as vehicle controls. The follicular protein (3 mg in 1 ml of 0.01 M PBS, pH 7) was administered (IM) at 07:00 hours and 19:00 hours beginning on day 1 of the menstrual cycle for a total of twenty-nine injections. Total dose for each monkey was 87 mg. Control monkeys received only PBS over the same interval. Iron supplement was administered once each week. Daily (09:00–11:00 hours), femoral blood samples (3.5 ml) were collected beginning with the onset of menses (day 1) and were continued until the onset of next menses. Radioimmunoassays for LH, FSH, 17$\beta$-estradiol, and progesterone in serum were performed.

Figure 35:
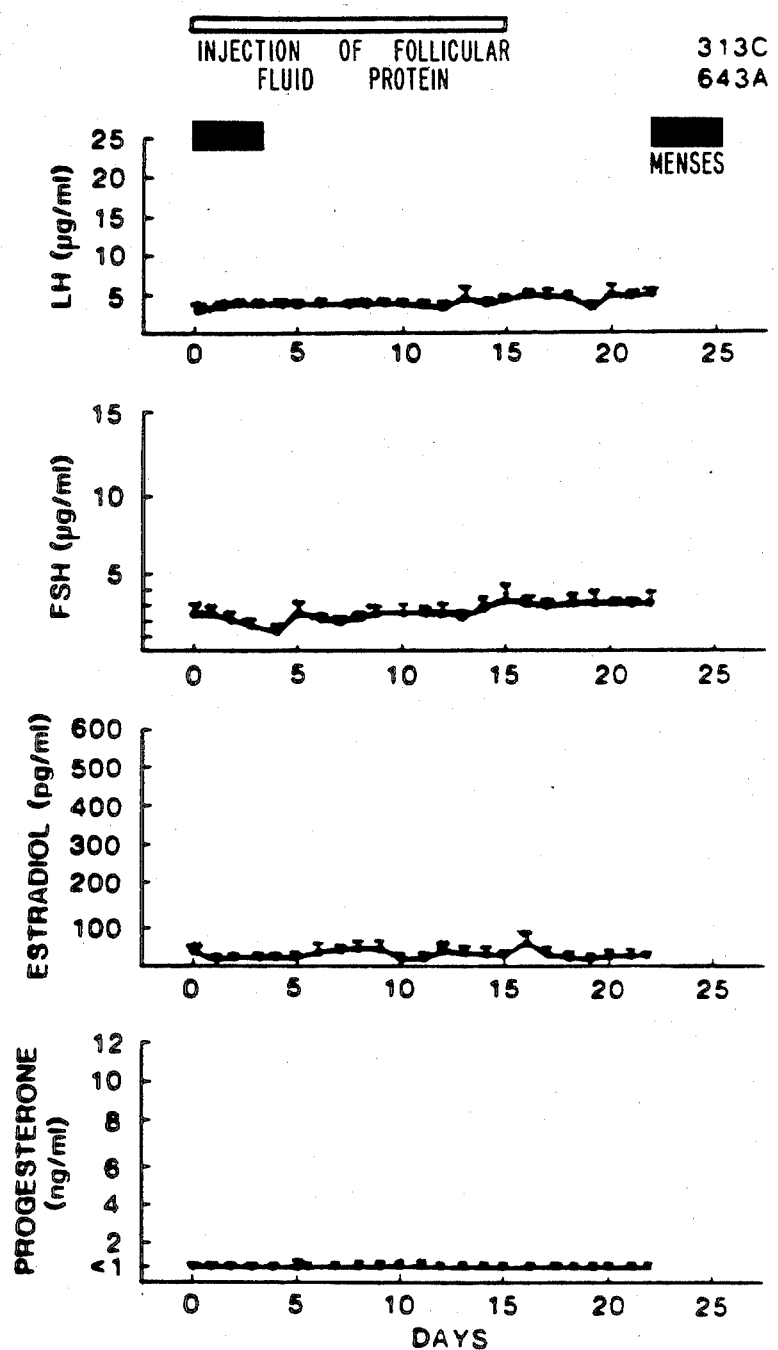
FIG. 35: Composite (X±SEM) of serum LH, FSH, estradiol, and progesterone levels from 2 rhesus monkeys which received twice daily injections (3 mg, intramuscularly) of a protein(s) partially purified from porcine follicular fluid which does not contain inhibin F activity. Bars indicate menses. Shaded area in each panel represents the 95% confidence intervals for the respective hormone levels determined for untreated normally cycling monkeys.
Figure 36:
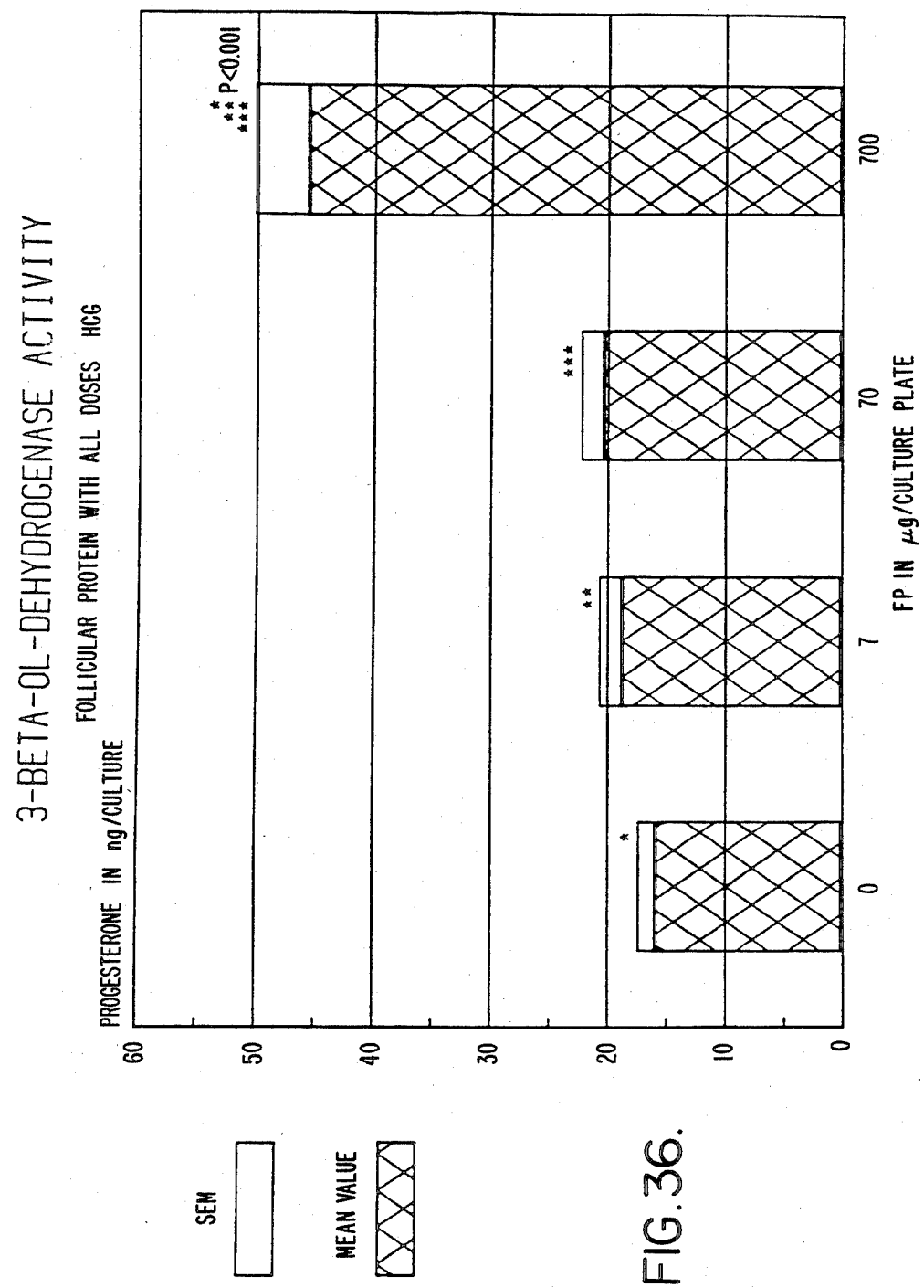
FIG. 36. Stimulation of 3β-ol dehydrogenase activity by porcine granulosa cells incubated with pregnenolone ($10^{-7}$M) for twenty-four hours in the presence of the follicular protein (0, 7, 70, 700 mg/culture).

Monkeys which received follicular protein injections had either no serum LH peak nor elevation of serum progesterone (n=2, FIG. 35), or a midcycle LH surge followed by an inadequate luteal phase as demonstrated by low serum progesterone levels and/or early onset (twenty-four days intermenstrual interval) of vaginal bleeding (n=2, FIG. 36). One follicular protein treated monkey had a midcycle LH surge followed by depressed follicular phase estradiol and luteal phase progesterone serum levels (not shown). The 95% confidence limits for the vehicle control and other values obtained for this population are depicted by the shaded area in FIGS. 35 and 36. Serum estradiol levels were reduced throughout the interval of FP treatment in the monkeys without LH surges (FIG. 35) in the late follicular phase (FIG. 36) in those with luteal phase defects. Serum FSH and LH levels were within the 95% confidence intervals for follicular protein treated monkeys (FIG. 36). However, in all five follicular protein treated monkeys, serum FSH levels rose during the course of therapy. In the monkeys with inadequate luteal phases (FIG. 36), serum estradiol levels were below the 95% confidence intervals in the late follicular and mid luteal phases. While the serum levels of both estradiol and progesterone were markedly suppressed after the LH surge. In subsequent cycles (N=3/monkey) onset of vaginal bleeding occurred in the usual twenty-six to thirty day monthly interval and no toxic effect of the follicular protein treatments was noted.

The follicular protein administered to normally cycling monkeys throughout the follicular phase of the menstrual cycle reduced peripheral estradiol levels without markedly affecting FSH, resulting in either apparent anovulation or inadequate luteal phases. The mixed response in serum sex steroid levels in the follicular protein treated monkeys may reflect a variable ovarian sensitivity to follicular protein. That serum FSH levels were not significantly inhibited indicates that this material has a biological activity different from that of charcoal-extracted whole porcine follicular fluid. Further, when follicular protein was tested in an inhibin assay, its activity was either at the limits of sensitivity or undetectable. Charcoal-extracted whole porcine follicular fluid containing inhibin disrupts the normal process of follicular maturation through selective inhibition of FSH secretion. In contrast, in the present Example, normal or rising serum FSH levels during follicular protein treatment were found. This indicates that the purification of follicular fluid described herein removed the major inhibin activity. The molecular weight of the described follicular protein is less than 20,000 while inhibin activity has been associated with molecular weights greater than 60,000.

The in vivo observations of reduced serum estradiol levels in follicular protein treated monkeys support the previously described Examples of granulosa cell aromatase inhibition by both human and porcine derived follicular protein. Further, these observations are in agreement with examples of reduced serum estradiol levels in follicular protein treated rats.

Luteal phase defects, as evidenced by suppressed serum estradiol and progesterone levels and early onset of vaginal bleeding, result from inadequate follicular maturation in the preceding follicular phase. Taken together with the observations reported in this Example of reduced serum estradiol and progesterone levels associated with follicular protein treatment these data indicate that the follicular protein described in the present invention has a direct intraovarian action which disrupts the normal process of folliculogenesis by an action apart from gonadotropin stimulation.

From the foregoing description, one skilled in the art can easily ascertain the essential characteristics of the invention and, without departing from the spirit and scope thereof, can adapt the invention to various usages and conditions. Changes in form and the substitution of equivalents are contemplated as circumstances may suggest or render expedient; and although specific terms have been employed herein, they are intended in a descriptive sense and not for purposes of limitation, the scope of the invention being delineated in the following claims.

TABLE 1

FF protein recovery and inhibition of rat ovarian weight in response to exogenous gonadotropin stimulation by the 10–55% SAS pooled hFF fraction developed through Dye-Matrix chromatography

| Dye-Matrix | Unbound | | Bound | |
| --- | --- | --- | --- | --- |
| | % Protein Recovered | % Inhibition[a] | % Protein Recovered | % Inhibition[a] |
| Control | 96 | 68 ± 3.2 | 4.6 | 0 |
| Blue A | 35 | 10 ± 4.7 | 63 | 0 |
| Blue B | 87 | 11 ± 8.1 | 21 | 14 ± 3.2 |
| Red A | 38 | 0 | 63 | 0 |
| Orange A | 86 | 0 | 17 | 89 ± 6.8[b] |
| Green A | 31 | 0 | 68 | 0 |

Bound material was eluted with 1.5 M KCl in Tris-HCl (0.025 M, pH 7.5).
[a]Values are the means ± SEM.
[b]Significantly greater inhibition of rat ovarian weight response to gonadotropin stimulation compared to other Dye-matrix eluents (P > 0.05, Student's t test).

TABLE 2

| Patient No. | Volume (ml) | Viable granulosa cells | Follicular fluid aspirate | | | |
|---|---|---|---|---|---|---|
| | | | Steroid conc. (ng/ml) | | | |
| | | | Estradiol | Estrone | Progesterone | 17-Hydroxy-progesterone |
| 1 | 12.0 | $1.0 \times 10^5$ | 396 | 37 | 12,377 | 212 |
| 2 | 7.1 | | 204 | 3 | 11,761 | 889 |
| 3 | 12.2 | $2.6 \times 10^5$ | 440 | 220 | 12,746 | 82 |
| 4 | 12.0 | $1.7 \times 10^5$ | 296 | | 10,132 | 176 |
| 5 | 5.3 | $0.75 \times 10^5$ | 327 | | 7,500 | 667 |
| 6 | 5.3 | $0.7 \times 10^5$ | 1,740 | 411 | 9,197 | 1,091 |
| 7 | 8.8 | $10.5 \times 10^5$ | 708 | 492 | 11,371 | 1,200 |

TABLE 3

Protein Recovery and Inhibition of Ovarian Weight Response From Dyematrix Chromatography of the 10–55% Saturated Ammonium Sulfate Dialyzed Porcine Follicular Fluid Fraction

| Dyematrix | Unbound | | Bound | |
|---|---|---|---|---|
| | % Protein | % Inhibition | % Protein | % Inhibition |
| CONTROL | 94 | 78 ± 6.1 | 8.8 | 0 |
| BLUE A | 34 | 22 ± 8.3 | 65 | 0 |
| BLUE B | 81 | 0 | 20 | 39 ± 7.4 |
| RED A | 33 | 12 ± 4.2 | 65 | 0 |
| ORANGE A | 88 | 0 | 13 | 84 ± 7.4 |
| GREEN A | 37 | 0 | 63 | 22 ± 3.8 |

*Significantly greater inhibition (p less than .05 Student's T) of hMG-induced rat ovarian weight response compared to other dye-ligand eluents.

The invention is claimed as follows:

1. A substantially purified follicular regulatory protein having the biological effect of inhibiting aromatase activity in a mammalian biological system, as defined by the extent of the conversion of androgens to estrogens in the essential absence of the inhibition of the level of FSH in said biological system.

2. The protein of claim 1 which has the further biological activity of stimulating the activity of 3-β-ol dehydrogenase in porcine granulosa cells.

3. The protein of claim 2 which has the further biological activity of inhibiting LH receptor function in porcine granulosa cells.

4. A purified follicular regulatory protein having the biological activity of:
   inhibiting aromatase activity as defined by the extent of the conversion of androgens to estrogens in the essential absence of the inhibition of the level of FSH in said biological system;
   stimulating the activity of 3-β-ol dehydrogenase in porcine granulosa cells;
   inhibiting LH receptor function in porcine granulosa cells; and
   inhibiting ovarian response to gonadotropins.

5. The protein of claim 4 which has a molecular weight of from about 5,500 to 18,000 daltons and an isoelectric point in the range of from about pH 3.5 to pH 7.0.

6. The protein of claim 4 which has a molecular weight of from about 10,000 to 18,000 daltons and an isoelectric point in the range of from about pH 4.5 to pH 6.5.

7. A purified follicular regulatory protein isolated from the group consisting of ovarian venous blood, follicular fluid and granulosa cell culture medium, and having the biological activity in a mammalian biological system of:
   inhibiting aromatase activity as defined by the extent of the conversion of androgens to estrogens in the essential absence of the inhibition of the level of FSH in said biological system;
   stimulating the activity of 3-β-ol dehydrogenase in porcine granulosa cells;
   inhibiting LH receptor function in porcine granulosa cells; and
   inhibiting ovarian response to gonadotropins.

8. The protein of claim 7 which has a molecular weight of from about 5,500 to 18,000 daltons and an isoelectric point in the range of from about pH 3.5 to pH 7.0.

9. The protein of claim 7 which has a molecular weight of from about 10,000 to 18,000 daltons and an isoelectric point in the range of from about pH 4.5 to pH 6.5.

* * * * *